US008088382B2

(12) United States Patent
Muller et al.

(10) Patent No.: US 8,088,382 B2
(45) Date of Patent: Jan. 3, 2012

(54) METHODS OF INHIBITING TRANSENDOTHELIAL MIGRATION OF NEUTROPHILS AND MONOCYTES WITH ANTI-CD99L2 ANTIBODIES

(75) Inventors: William A. Muller, Port Washington, NY (US); Alan R. Schenkel, Ft. Collins, CO (US)

(73) Assignee: Cornell Research Foundation, Inc., Ithaca, NY (US)

( * ) Notice: Subject to any disclaimer, the term of this patent is extended or adjusted under 35 U.S.C. 154(b) by 777 days.

(21) Appl. No.: 11/994,363

(22) PCT Filed: Jun. 30, 2006

(86) PCT No.: PCT/US2006/026084
§ 371 (c)(1),
(2), (4) Date: Dec. 31, 2007

(87) PCT Pub. No.: WO2007/005898
PCT Pub. Date: Jan. 11, 2007

(65) Prior Publication Data
US 2008/0213279 A1 Sep. 4, 2008

Related U.S. Application Data

(60) Provisional application No. 60/697,064, filed on Jul. 5, 2005.

(51) Int. Cl.
*A61K 39/395* (2006.01)
(52) U.S. Cl. ............... 424/153.1; 424/130.1; 424/133.1; 424/141.1; 424/143.1; 424/152.1; 424/172.1; 424/173.1
(58) Field of Classification Search ........................ None
See application file for complete search history.

(56) References Cited

U.S. PATENT DOCUMENTS

| 4,631,211 A | 12/1986 | Houghten |
| 4,736,866 A | 4/1988 | Leder et al. |
| 4,849,222 A | 7/1989 | Broaddus |
| 4,870,009 A | 9/1989 | Evans et al. |
| 4,946,778 A | 8/1990 | Ladner et al. |
| 4,959,317 A | 9/1990 | Sauer |
| 4,980,286 A | 12/1990 | Morgan et al. |
| 5,010,175 A | 4/1991 | Rutter et al. |
| 5,091,309 A | 2/1992 | Schlesinger et al. |
| 5,100,669 A | 3/1992 | Hyon et al. |
| 5,132,405 A | 7/1992 | Huston et al. |
| 5,168,062 A | 12/1992 | Stinski |
| 5,385,839 A | 1/1995 | Stinski |
| 5,459,127 A | 10/1995 | Felgner et al. |
| 5,476,786 A | 12/1995 | Huston |
| 5,580,859 A | 12/1996 | Felgner et al. |
| 5,589,466 A | 12/1996 | Felgner et al. |
| 5,616,491 A | 4/1997 | Mak et al. |
| 5,635,493 A | 6/1997 | Vournakis et al. |
| 5,654,168 A | 8/1997 | Bujard et al. |
| 5,777,195 A | 7/1998 | Fienberg et al. |
| 5,801,030 A | 9/1998 | McVey et al. |
| 7,223,395 B2 | 5/2007 | Muller et al. |
| 2003/0211099 A1* | 11/2003 | Muller et al. ............... 424/144.1 |

FOREIGN PATENT DOCUMENTS

| CA | 2 012 311 A1 | 9/1990 |
| WO | 89/12690 | 12/1989 |
| WO | 92/00252 | 1/1992 |
| WO | 92/05263 A1 | 4/1992 |
| WO | 92/06180 | 4/1992 |
| WO | 92/20316 | 11/1992 |
| WO | 92/22635 | 12/1992 |
| WO | 93/07861 | 4/1993 |
| WO | 93/14188 | 7/1993 |
| WO | 94/21807 A1 | 9/1994 |
| WO | 94/28028 | 12/1994 |
| WO | 95/11010 | 4/1995 |
| WO | 95/18863 | 7/1995 |
| WO | 95/21931 | 8/1995 |
| WO | 95/28494 | 10/1995 |
| WO | 96/17823 | 6/1996 |
| WO | 96/25508 | 8/1996 |
| WO | WO-96/27613 A1 | 9/1996 |
| WO | 98/06237 | 2/1998 |
| WO | 99/01157 A1 | 1/1999 |
| WO | 99/01158 A1 | 1/1999 |

(Continued)

OTHER PUBLICATIONS

Suh et al., Gene 307: 63-76, 2003.*
Suh et al., Gene 63-76, 2003.*
Bixel et al., Blood 109: 5327-5336, 2007.*
"U.S. Appl. No. 10/221,758, Amendment After Allowance filed Jan. 24, 2007", 4 pgs.
"U.S. Appl. No. 10/221,758, Amendment and Response filed Jun. 6, 2006 to Non-Final Office Action mailed Mar. 10, 2006", 11 pgs.
"U.S. Appl. No. 10/221,758, Amendment and Response filed Oct. 19, 2006 to Final Office Action mailed Aug. 23, 2006", 8 pgs.

(Continued)

*Primary Examiner* — Phillip Gambel
(74) *Attorney, Agent, or Firm* — Schwegman, Lundberg & Woessner P.A.

(57) ABSTRACT

The present invention provides methods and compositions for modulating transendothelial migration (TEM) of leukocytes. In particular, inhibition of TEM can provide a potent therapeutic approach to treating inflammatory conditions. The invention specifically relates to the discovery that the adhesion molecule CD99L2 mediates TEM of leukocytes. CD99L2 is present on endothelial cells and leukocytes and mediates leukocyte-endothelial cell adhesion. Blockade of CD99L2 by use of a specific antibody blocks migration of leukocytes into a site of inflammation. CD99L2 shows functional analogy to the structurally-related molecule, CD99, inhibition of which, in conjunction with inhibition of PECAM, causes near total blockade of TEM. Thus, blocking CD99L2 on either endothelial cells or monocytes can block migration 80-90%. In conjunction with PECAM inhibitors, TEM blockade can approach 100%. Therapeutic treatments involving inhibition of CD99L2 show significant promise in remediation of inflammatory conditions.

22 Claims, 14 Drawing Sheets

FOREIGN PATENT DOCUMENTS

WO    WO-01/68131 A1    9/2001

OTHER PUBLICATIONS

"U.S. Appl. No. 10/221,758, Final Office Action mailed Aug. 23, 2006", 5 pgs.
"U.S. Appl. No. 10/221,758, Final Office Action mailed Nov. 17, 2005", 9 pgs.
"U.S. Appl. No. 10/221,758, Non-Final Office Action Jun. 1, 2005", 9 pgs.
"U.S. Appl. No. 10/221,758, Non-Final Office Action mailed Jan. 12, 2005", 5 pgs.
"U.S. Appl. No. 10/221,758, Non-Final Office Action mailed Mar. 10, 2006", 6 pgs.
"U.S. Appl. No. 10/221,758, Notice of Allowance mailed Nov. 27, 2006", 6 pgs.
"U.S. Appl. No. 10/221,758, Preliminary Amendment filed Jan. 31, 2003", 80 pgs.
"U.S. Appl. No. 10/221,758, Response filed Feb. 17, 2006 to Final Office Action mailed Nov. 17, 2005", 12 pgs.
"U.S. Appl. No. 10/221,758, Response filed Mar. 25, 2005 to Restriction Requirement mailed Feb. 25, 2005", 4 pgs.
"U.S. Appl. No. 10/221,758, Response filed Oct. 3, 2005 to Non-Final Office Action mailed Jun. 1, 2005", 13 pgs.
"U.S. Appl. No. 10/221,758, Restriction Requirement mailed Feb. 25, 2005", 5 pgs.
"Canadian Application Serial No. 2,402,530, Response filed Jun. 30, 2010 to Office Action mailed Jan. 6, 2010", 8 pgs.
"Canadian Application Serial No. 2402530, Office Action mailed Jan. 6, 2010", 2 Pgs.
"European Application Serial No. 01920325.6, Communication mailed Apr. 13, 2006", 4 pgs.
"European Application Serial No. 01920325.6, Response filed Aug. 15, 2006 to Communication mailed Apr. 13, 2006", 4 pgs.
"European Application Serial No. 01920325.6, Summons to Attend Oral Proceedings Received mailed Mar. 2, 2010", 4 pgs.
"European Application Serial No. 01920325.6, Supplementary Partial European Search Report mailed Feb. 26, 2003", 4 pgs.
"International Application Serial No. PCT/US01/07963, International Preliminary Examination Report completed Jul. 22, 2002", 4 pgs.
"International Application Serial No. PCT/US01/07963, International Search Report mailed Jun. 8, 2001", 1 pg.
"International Application Serial No. PCT/US06/26084, International Search Report mailed May 2, 2007", 1 pg.
"International Application Serial No. PCT/US06/26084, Written Opinion mailed May 2, 2007", 5 pgs.
"Making and using antibodies", [online]. [archived Oct. 27, 2007]. Retrieved from the Internet: //web.archive.org/web/20071027101031/.//www-users.med.cornell.edu/~jawagne/Antibody_Approaches.html>, (May 31, 2005), 2 pgs.
Aubrit, F., et al., "The biochemical characterization of E2, a T cell surface molecule involved in rosettes", *Eur. J. Immunol.*, 19, (1989), 1431-1436.
Aussel, C., et al., "Sphingosine, oleylamine and stearylamine inhibit both CD11A/CD18-dependent and -independent homotypic aggregation: demonstration by cytofluorimetry", *Immunology Letters*, 47, (1995), 175-180.
Banting, G. S., et al., "The *MIC2* Gene Product: Epitope Mapping and Structural Prediction Analysis Define an Integral Membrane Protein", *Molecular Immunology*, 26(2), (1989), 181-188.
Bernard, G., et al., "Apoptosis of Immature Thymocytes Mediated by E2/CD99", *The Journal of Immunology*, 158, (1997), 2543-2550.
Bernard, G., et al., "The E2 Molecule (CD99) Specifically Triggers Homotypic Aggregation of CD4+ CD8+ Thymocytes", the Journal of Immunology, 154, (1995), 26-32.
Bixel, G. M., et al., "CD99 and CD99L2 act at the same cite as, but independently of, PECAM-1 durring leukocyte diapedesis", *Blood First Edition Paper*, prepublshed online May 17, 2010, DOI: 10.1182/Blood/2009-12-256388, (May 17, 2010), 33 pgs.
Bixel, G., et al., "Mouse CD99 participates in T-Cell recruitment into inflamed skin", *Blood*,104(10), (2004), 3205-3213.
Carman, C. V., et al., "A transmigratory cup in leukocyte diapedesis both through invidual vascular endothelial cells and beween them", *The Journal of Cell Biology*, 167(2), (2004), 378-388.
Choi, E. Y., et al., "Engagement of CD99 Induces Up-Regulation of TCR and MHC Class I and II Molecules on the Surface of Human Thymocytes", *The Journal of Immunology*, 161, (1998), 749-754.
Dufour, E. M., et al., "CD99 Is Essential for Leukocyte Diapedesis in Vivo", *Cell Communication and Adhesion 15*, (2008), 351-363.
Dworzak, M. N., et al., "Flow Cytometric Assessment of Human MIC2 Expression in Bone Marrow, Thymus, and Peripheral Blood", *Blood*, 83(2), (1994), 415-425.
Ellis, N. A., et al., "PBDX is the XG blood group gene", *Nature Genetics*, 8, (1994), 285-290.
Gelin, C., et al., "The E2 antigen, a 32 kd glycoprotein involved in T-cell adhesion processes, is the MIC2 gene product", *The EMBO Journal*, 8(11), (1989), 3253-3259.
Hahn, J.-H., et al., "CD99 (*MIC2*) Regulates the LFA-1/ICAM-1-Mediated Adhesion of Lymphocytes, and Its Gene Encodes Both Positive and Negative Regulators of Cellular Adhesion", *The Journal of Immunology*, 159, (1997), 2250-2258.
Hale, L. P., et al., "Bromelan Treatment of Human T Cells Removes CD44, CD45RA, E2/MIC2, CD6, CD7, CD8, and Leu 8/LAM1 Surface Molecules and Markedly Enhances CD2-Mediated T Cell Activation", *The Journal of Immunology*, 149(12), (1992), 3809-3816.
Lee, G. K., et al., "LFA-1- and ICAM-1-dependent Homotypic Aggregation of Human Thymocytes Induced by JL1 Engagement", *Molecules and Cells*, 9(6), (1999), 662-667.
Lou, Olivia, et al., "CD99 Is a Key Mediator of the Transendothelial Migration of Neutrophils", *The Journal of Immunology*, 178, (2007), 1136-1143.
Norman, M. U, et al., "Therapeutic Intervention in Inflammatory Diseases: A Time and Place for Anti-Adhesion Therapy", *Microcirculation*, 12(1), (2005), 91-98.
Park, C. K., et al., "High CD99 Expression in Memory T and B Cells in Reactive Lymph Nodes", *J. Korean Med. Sci.*, 14, (1999), 600-606.
Park, H. P., "Rapid divergency of rodent CD99.orthologs: Implications for the evolution of the pseudoautosomal region", *Gene*, 353, (2005), 177-188.
Petit, C., et al., "Physical mapping of the human pseudo-autosomal region; comparison with genetic linkage map", *The EMBO Journal*, 7(8), (1988), 2369-2376.
Schenkel, A. R, et al., "CD99 Plays a Major Role in the Migration of Monocytes Through Endothelial Junctions", *Nature Immunology*, 3(2), (Jan. 2002), 143-150.
Sherman-Gold, R., "Companies pursue therapies based on complex cell adhesion molecules", *Genetic Engineering News*, 13(13), (Jul. 1993), 6-7.
Smith, M. J., et al., "The genomic organisation of the human pseudoautosomal gene *MIC2* and the detection of a related locus", *Human Molecular Genetics*, 23(4), (1993), 417-422.
Waclavicek, M., et al., "CD99 Engagement on Human Peripheral Blood T Cells Results in TCR/CD3-Dependent Cellular Activation and Allows for Th1-Restricted Cytokine Production", *The Journal of Immunology*, 161, (1998), 4671-4678.
Wingett, D., et al., "A Role for CD99 in T Cell Activation", *Cellular Immunology*, 193, (1999), 17-23.
Shang, X. Z. and A. C. Issekutz. "Contribution of CD11a/CD18, CD11b/CD18, ICAM-1 (CD54) and -2 (CD102) to human monocyte migration through endothelium and connective tissue fibroblast barriers," Eur. J. Immunol., 1998, 28:1970-1979.
Issekutz, A.C., et al., "Role of ICAM-1 and ICAM-2 and alternate CD11/CD18 ligands in neutrophil transendothelial migration," J. Leuk. Biol., 1999, 65:117-126.
Xie, Y. and W. A. Muller. "Molecular cloning and adhesive properties of murine platelet/endothelial cell adhesion molecule-1," Proc. Natl. Acad. Sci. USA, 1993, 90:5569-5573.
Kostrikis, L.G., et al., "A chemokine receptor CCR2 allele delays HIV-1 disease progression and is associated with a CCR5 promoter mutation," Nat. Med., 1998, 4:350-353.
McElrath, M.J., et al., "Cutaneous leishmaniasis. The defect in T cell influx in BALB/c mice," J. Exp. Med., 1987, 165:546-559.

Smith, C. W., et al., "Chemotactic factors regulate lectin adhesion molecule 1 (LECAM-1)-dependent neutrophil adhesion to cytokine-stimulated endothelial cells in vitro," J. Clin. Invest., 1991, 87:609-618.

Muller, W. A., et al., "The membrane proteins of the vacuolar system. II. Bidirectional flow between secondary lysosomes and plasma membrane," J. Cell Biol., 1980, 86:304-314.

Muller, W.A. and M.A. Gimbrone Jr. "Plasmalemmal proteins of cultured vascular endothelial cells exhibit apical-basal polarity: Analysis by surface-selective iodination," J. Cell Biol., 1986, 103:2389-2402.

Pober, J.S., et al., "Two distinct monokines, interleukin 1 and tumor necrosis factor, each independently induce biosynthesis and transient expression of the same antigen on the surface of cultured human vascular endothelial cells." J. Immunol., 1996, 136:1680-1687.

Romer, L.H., et al., "IFN-gamma and TNF-alpha induce redistribution of PECAM-1 [CD31] on human endothelial cells," J. Immunol., 1995, 154:6582-6592.

Aruffo, A. and B. Seed. "Molecular cloning of CD28 cDNA by a high-efficiency COS cell expression system," Proc. Natl. Acad. Sci. USA, 1987, 84:8573-8577.

Seed, B. and A. Aruffo. "Molecular cloning of the CD2 antigen, the T-cell erythrocyte receptor, by a rapid immunoselection procedure," Proc. Natl. Acad. Sci. USA, 1987, 84:3365-3369.

Muller, W.A., et al., "A heterophilic adhesion mechanism for Platelet/Endothelial Cell Adhesion Molecule-1 [CD31]," J. Exp. Med., 1992, 175:1401-1404.

Huang, A.J., et al., "Endothelial cell cytosolic free calcium regulates neutrophil migration across monolayers of endothelial cells," J. Cell Biol., 1993, 120:1371-1380.

Divirgilio, F., et al., "Fura-2 secretion and sequestration in macrophages," J. Immunol., 1988, 140:915-920.

Galfre, G., et al., "Antibodies to major histocompatibility antigens produced by hybrid cell lines," Nature, 1977, 266:550-552.

Mishell, B.B. and S.M. Shiigi. "Selected methods in cellular immunology," W.H.Freeman, San Francisco, 1980. Contents, pp. VII-XIV only.

Reilly, P.L. et al., "The native structure of intercellular adhesion molecule-1 (ICAM-1) is a dimer. Correlation with binding to LFA-1," J. Immunol., 1995, 155:529-532.

Miller, J., et al., "Intercellular adhesion molecule-1 dimerization and its consequences for adhesion mediated by lymphocyte function associated molecule-1," J. Exp. Med., 1995, 182:1231-1241.

Mizgerd, J.P., et al., "Neutrophil emigration in the skin, lungs, and peritoneum: Different requirements for CD11/CD18 revealed by CD18-deficient mice," J. Exp. Med., 1997, 186:1357-1364.

Mayadas, T.N., et al., "Leukocyte rolling and extravasation are severely compromised in P selectin-deficient mice," Cell, 1993, 74:541-554.

Watson, S.R., et al., "Neutrophil influx into an inflammatory site inhibited by a soluble homing receptor-IgG chimaera," Nature (London), 1991, 349:164-167.

Muller, W.A., et al., "A human endothelial cell-restricted, externally disposed plasmalemma protein enriched in intercellular junctions," J. Exp. Med., 1989, 170, 399-414.

Muller, W.A., et al., "A heterophilic adhesion mechanism for platelet/endothelial cell adhesion molecule-1 (CD31)," J. Exp. Med., 1992, 175:1401-1404.

Schenkel, A.R., et al., "CD99 plays a major role in the migration of monocytes through endothelial junctions," Nature Immunol., 2002, 3:143-150.

"Canadian Application Serial No. 2,402,530, Office Action mailed Jun. 29, 2011", 2 pgs.

"European Application Serial No. 01920325.6, Amended Set of Claims filed Sep. 6, 2010", 22 pgs.

"European Application Serial No. 01920325.6, Response filed Aug. 18, 2010 to Summons to Attend Oral Proceedings mailed Mar. 2, 2010", 37 pgs.

Kumar, V., et al., "", Robbins and Cotran: Pathologic Basis of Disease, Eighth Edition, Saunders, (2010), 50-51, 68-71.

Schenkel, Alan R, et al., "Platelet endothelial cell adhesion molecule deficiency or blockade significantly reduces leukocyte emigration in a majority of mouse strains.", J Immunol., 173(10), (Nov. 15, 2004), 6403-8.

Seidman, M. A, et al., "PECAM-independent thioglycollate peritonitis is associated with a locus on murine chromosome 2", PLoS One, 4(1), (2009), e4316.

Muller, W.A., et al., "PECAM-I is Required for Transendothelial Migration of Leukocytes," J. Exp. Med., 1993, 178:449-460.

Bogen, S., et al., "Monoclonal Antibody to Murine PECAM-I [CD31] Blocks Acute Inflammation In Vivo," J. Exp. Med. 179: 1059-1064, 1994.

Berman, M. E. and W. A. Muller. "Ligation of platelet/endothelial cell adhesion molecule 1 (PECAM-1/CD31) on monocytes and neutrophils increases binding capacity of leukocyte CR3 (CD11b/CD18)," J. Immunol., 1995, 154:299-307.

Liao, F., et al. "Migration of monocytes across endothelium and passage through extracellular matrix involve separate molecular domains of PECAM-1," J. Exp. Med., 1995, 182:1337-1343.

Berman, M. E., et al., "Roles of platelet/endothelial cell adhesion molecule-1 (PECAM-1, CD31) in natural killer cell transendothelial migration and beta 2 integrin activation," J. Immunol., 1996, 156:1515-1524.

Liao, F., et al., "Soluble domain 1 of platelet-endothelial cell adhesion molecule (PECAM) is sufficient to block transendothelial migration in vitro and in vivo.," J. Exp. Med., 1997, 185:1349-1357.

Muller, W. A., et al., "Transendothelial migration and interstitial migration of monocytes are mediated by separate domains of monocyte CD31." In Leukocyte Typing VI. Proceedings of the VIth International Leukocyte Differentiation Antigen Workshop, Kobe, Japan, 1996. T. Kishimoto, editor. Garland Publishers, London. 370-372.

Vaporciyan, A. A., et al., "Involvement of platelet-endothelial cell adhesion molecule-1 in neutrophil recruitment in vivo," Science, 1993 262:1580-1582.

Wakelin, M. W., et al., "An anti-platelet/endothelial cell adhesion molecule-1 antibody inhibits leukocyte extravasation from mesenteric microvessels in vivo by blocking the passage through basement membrane," J. Exp. Med., 1996, 184:229-239.

Murohara, T., et al., "Blockade of platelet endothelial cell adhesion molecule-1 protects against myocardial ischemia and reperfusion injury in cats," J. Immunol., 1996, 156:3550-3557.

Christofidou-Solomidou, M., et al., "Neutrophil platelet endothelial cell adhesion molecule-1 participates in neutrophil recruitment at inflammatory sites and is down-regulated after leukocyte extravasation," J. Immunol., 1997, 158:4872-4878.

Gumina, R. J., et al., "Antibody to platelet/endothelial cell adhesion molecule-1 reduces myocardial infarct size in a rat model of ischemia-reperfusion injury," Circulation, 1996, 94:3327-3333.

Ross, R., "The pathogenesis of atherosclerosis: a perspective for the 1990s," Nature, 1993, 362:801-809.

Lasky, L. A., "Selectins: Interpreters of cell-specific carbohydrate information during inflammation," Science, 1992, 258:964-969.

Springer, T. A., "Traffic signals for lymphocyte recirculation and leukocyte emigration: The multistep paradigm," Cell, 1994, 76:301-314.

Lo, S. K., et al., "Endothelial-leukocyte adhesion molecule 1 stimulates the adhesive activity of leukocyte integrin CD3 [CD11B/CD18, Mac-1, alpha m beta 2] on human neutrophils," J. Exp. Med., 1991, 173:1493-1500.

Lorant, D. E. et al., "Coexpression of GMP-140 and PAF by endothelium stimulated by histamine or thrombin: A juxtacrine system for adhesion and activation of neutrophils," J. Cell Biol., 1991, 115:223-234.

Hermanowski-Vosatka, A., et al., "Integrin modulating factor-1: A lipid that alters the function of leukocyte integrins," Cell, 1992, 68:341-352.

Tanaka, Y., et al., "T-cell adhesion induced by proteoglycan-immunobilized cytokine MIP-1 beta," Nature, 1993, 361:79-82.

Huber, A. R., et al., "Regulation of transendothelial neurophil migration by endogenous interleukin-8," Science, 1991, 254:99-102.

Tanaka, Y., et al., "CD31 expressed on distinctive T cell subsets is a preferential amplifier of beta1 integrin-mediated adhesion," J. Exp. Med., 1992, 176:245-253.

Piali, L., et al., "Murine platelet endothelial cell adhesion molecule (PECAM-1/CD31) modulates beta2 integrins on lymphokine-activated killer cells," Eur. J. Immunol., 1993, 23:2464-2471.

Meerschaert, J. and M. B. Furie. "Monocytes use either CD11/CD18 or VLA-4 to migrate across human endothelium in vitro," J. Immunol., 1994, 152:1915-1926.

Newman, P. J., et al., "PECAM-1 [CD31] cloning and relation to adhesion molecules of the immunoglobulin gene superfamily," Science, 1990, 247:1219-1222.

Sun, Q.-H., et al., "Individually distinct Ig homology domains in PECAM-1 regulate homophilic binding and modulate receptor affinity." J. Biol. Chem., 1996, 271:11090-11098.

Duncan, G. S., et al., "Genetic evidence for functional redundancy of platelet/endothelial cell adhesion molecule-1 (PECAM-1): CD31-deficient mice reveal PECAM-1-dependent and PECAM-1-independent functions," J. Immunol., 1999, 162:3022-3030.

Tang, Q. and R. L. Hendricks, "Interferon gamma regulates platelet endothelial cell adhesion molecule-1 expression and neutrophil infiltration into herpes simplex virus-infected mouse corneas." J Exp Med., 1996, 184:1435-1447.

Feng, D., et al., "Neutrophils emigrate from venules by a transendothelial cell pathway in response to fMLP," J. Exp. Med., 1998, 187:903-915.

Ali J. et al., "Vascular endothelial cadherin (VE-Cadherin): Cloning and role in endothelial cell-cell adhesion," 1997, Microcirculation 4:267-277.

Lampugnani, M.G., et al., "A novel endothelial-specific membrane protein is a marker of cell-cell contacts," J. Cell. Biol., 1992, 118:1511-1522.

Gotsch, U., et al., "VE-cadherin antibody accelerates neutrophil recruitment in vivo." J. Cell Sci., 1997, 110:583-588.

De Fougerolles, A. R., et al., "Characterization of ICAM-2 and evidence for a third counter-receptor for LFA-1," J. Exp. Med., 1991, 174:253-267.

Xu, H., et al., "Isolation, characterization, and expression of mouse ICAM-2 complementary and genomic DNA," J. Immunol., 1992, 149:2650-2655.

Xie, J., et al., "Intercellular adhesion molecule-2 (CD102) binds to the leukocyte integrin CD11b/CD18 through the A domain," J. Immunol., 1995, 155:3619-3628.

Martin-Padura, I., et al., "Junctional adhesion molecule, a novel member of the immunoglobulin superfamily that distributes at intercellular junctions and modulates monocyte transmigration," J. Cell Biol., 1998, 142:117-127.

Naik, U. P., et al., "Mechanisms of platelet activation by a stimulatory antibody: Cross-linking of a novel platelet receptor for monoclonal antibody F11 with the FcgammaRII receptor," 1995, Biochem. J. 310:155-162.

Furuse, M., et al., "Occludin: A novel integral membrane protein localizing at tight junctions," J. Cell Biol., 1993, 123:1777-1788.

McCarthy, K. M., et al., "Occludin is a functional component of the tight junction." J. Cell Sci., 1996, 109:2287-2298.

Fujimoto, K., "Freeze-fracture replica electron microscopy combined with SDS digestion for cytochemical labeling of integral membrane proteins. Application to the immunogold labeling of intercellular junctional complexes," J. Cell Sci., 1995, 108:3443-3449.

Saitou, M. et al. "Occludin-deficient embryonic stem cells can differentiate into polarized epithelial cells bearing tight junctions," J. Cell Biol., 1998, 141:397-408.

Furuse, M. et al., "Claudin-1and -2: Novel integral membrane proteins localizing at tight junctions with no sequence similarity to occludin," J. Cell Biol., 1998, 141:1539-1550.

Morita, K., et al., "Claudin-11/OSP-based tight junctions of myelin sheaths in brain and sertoli cells in testis," J. Cell Biol., 1999, 145:579-588.

Morita, K., et al. "Claudin multigene family encoding four-transmembrane domain protein components of tight junction strands," Proc. Natl. Acad. Sci. USA, 1999, 96:511-516.

Muller, W. A., "Transendothelial migration of leukocytes. In Leukocyte recruitment in inflammatory disease," G. Peltz, editor. R.G. Landis Company, 1996, Austin, TX. 3-18.

Muller, W. A. and S. Weigl. "Monocyte-selective transendothelial migration: Dissection of the binding and transmigration phases by an in vitro assay," J. Exp. Med., 1992, 176:819-828.

Butcher, E. C., "Leukocyte-endothelial cell recognition: three (or more) steps to specificity and diversity," Cell, 1991, 67:1033-1036.

Carlos, T.M. and J.M. Harlan. "Leukocyte-Endothelial Cell Adhesion Molecules," Blood, 1994, 84:2068-2101.

Muller, W. A., et al., "A human endothelial cell-restricted, externally disposed plasmalemmal protein enriched in intercellular junctions," J. Exp. Med., 1989, 170:399-414.

Albelda, S.M., et al., "Molecular and cellular properties of PECAM-1 [endoCAM/CD31]: A novel vascular cell-cell adhesion molecule," J. Cell Biol., 1991, 114:1059-1068.

Muller, W.A. "PECAM-1: an adhesion molecule at the junctions of endothelial cells." In Mononuclear Phagocytes. The Proceedings of the Fifth Leiden Meeting on Mononuclear Phagocytes. R. van Furth, Z. A. Cohn, and S. Gordon, editors. Blackwell Publishers, 1992, London. 138-148.

"Chinese Application Serial No. 200680024804, First Office Action mailed Apr. 27, 2011", (w/ English Translation), 12 pgs.

Suh, Y. H., et al., "Cloning, genomic organization, alternative transcripts and expression analysis of *CD99L2*, a novel paralog of human *CD99*, and identification of evolutionary conserved motifs", *Gene*, 307(1), (2003), 63-76.

"Chinese Application Serial No. 200680024804.9, Response filed Sep. 6, 2011 to Office Action mailed April 27, 2011", (w/ English Translation of Amended Claims), 15 pgs.

\* cited by examiner

Fig. 1 cDNA Sequence of muCD99L2

AGTAGAAATGCTCCCAGCC

ATG GTG GCC AGG CTC ACG GCT TTC CTC GTT TGC CTC GTT TTC TCC TTG GCC
ACC CTT GTC AGA GAA ACT GGA GAC ACA CAG GAT AGA GAT GGT TTT AAT CTG GAG GAT
GCA CTG AAA GAA AGG TCC GTA ACC AGA GCC CCA GCA AAT CAC CCA AGC ACC
ACG ACT AGG AGG CCA GTA ACA ACT ACA ACT AGA ACT AGG ACA GGA ACA GAG AGA
TGG GAC CAT GTT GCC ATG GAA CTA GAT GGG TTT GAC TTG GAA GAT GCC TTG GAT
CCA TCA AAT CCT GAT CTA GAT CCC AAA AAG CCA AGT GCA GGA GAA GCA GGA
GAT CGA AAT GAC CTT GAA CTT GAA ATC GTG GAA GAC ATT GTG GGT GGA TAC AAA
GGT TGG TCA AAG AAA GGC GGT TAT GGC AGC AGT GGT AAC GAT GCC CCT GGA
CCT GAC AAG AAA ACA GAA ACT GCA GAA ATT GCA GAT GTG GCC AGT GCC CTT
TCT GGC ATA TCG ACA GCT GTA TCC GGC CTC AAT GCA TAC TCC CAG CAG AAG
GCT ATG GCC CTG ATT CAG CAG CCC GAG GAG CCA TAC GTG ACA TAC TCA AAA
AAG TTT TGC TTC AGC GCT GTT TGT GAG GAG CCC CAA CCC CAA CCC CGG ATT TGA
GAG AAC CTG GAA ACG CAG TCT GCA GAA CCC CCA CCA GAG CCA CCC CGG ATT TGA
CAA GAA ACG CAG TCT GCA GAA CCC CCA CCA GAG CCA CCC CGG ATT TGA

GGCAGGTACATCTGAAGGAAGCCACCGCTTGTGACCCAGCTCCGGATTTCATTTGCCAAT
CCTTTCCCAAGTTTCTTCCCATGCCACTGGCTTATTGTAGTGAGTTTTCTGGAC
AAAAAAAAAAAAAAAAA

Fig. 2. Predicted Amino Acid Sequence of muCD99L2

```
            1 [                                                                .  60
1 muCD99L2    MVARLTAFLVCLVFSLATLVQRGYGDTDGFNLEDALKETSSVKQRWDHFSTTTRRPVTTR
2 CD99        -MARGAALALLFGLLGVLVAAPDG---GFDLSDALPDNENKKP-----------------
consensus/100% hARhsAhhlhLhh.LusLVtts.G....GFsLpDAL.-spshK.................
           61                                .                                . 120
1 muCD99L2    APANPAERWDHVATTTRRPGTTRAPSNPMELDGFDLEDALDDRNDLDGPKKPSAGEAGG
2 CD99        -------------------------TAIPKKPSAGDDFDLGDAVVDGEDDPNPNHPSSSGS
consensus/100%                            TthPppP.thDsFDLtDAlsDtpDhssPp.spsupuGu
          121                                .                                . 180
1 muCD99L2    WSDKDLEDIVEGGGYKPDKNKGGGGYGSNDDPGSGISTETGTIAGVASALAMALIGAVSS
2 CD99        FSDADLADGVSGGEGKGGSDGGGSHRKEGEEADAP------GVIPGIVGAVVVAVAGAISS
consensus/100%aSDtDLtDhVpGGthKsspstGGuthtps--ssus......GsIsGlsuAlshAlhgAISS
          181                                .                                ] 237
1 muCD99L2    YISYQQKKFCFSIQQGLNADYVKGENLEAVVCEEPQVTYSKQETQSAEPPPEPPRI
2 CD99        FIAYQKKKLCFkeQGEVDMESHRNANAEPAV-------------------------
consensus/100%aIuYQpKKhCFp.Qttlsh-.h+stNhEssV.........................
``` h = HYDROPHOBIC  
l = ALIPHATIC  
t = TURNLIKE  
a = AROMATIC  
+ = POSITIVE CHARGE  
c = CHARGED s = SMALL  
u = TINY  
p = POLAR  
- = NEGATIVE CHARGE  
o = ALCOHOL

Fig. 3
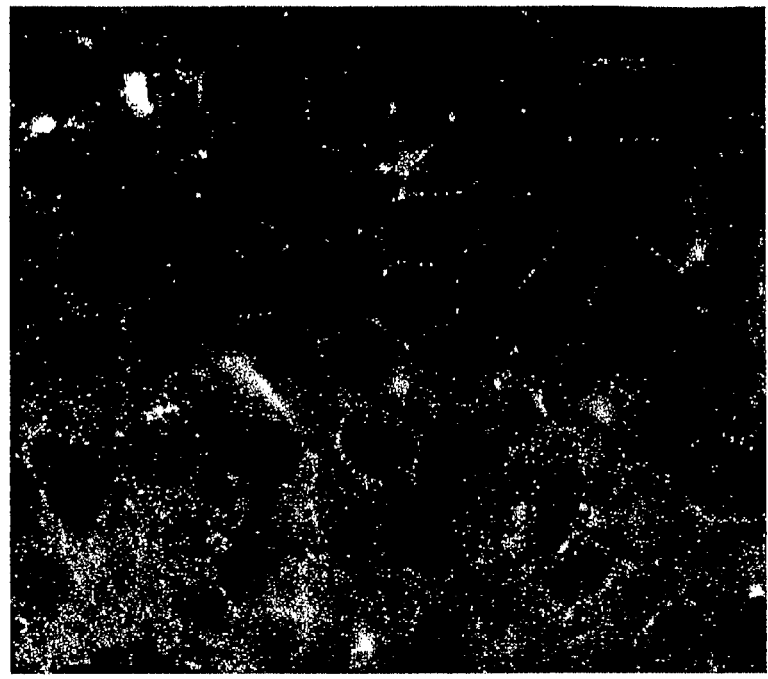
Rabbit anti-muCD99L2
Preimmune Serum

Fig. 7
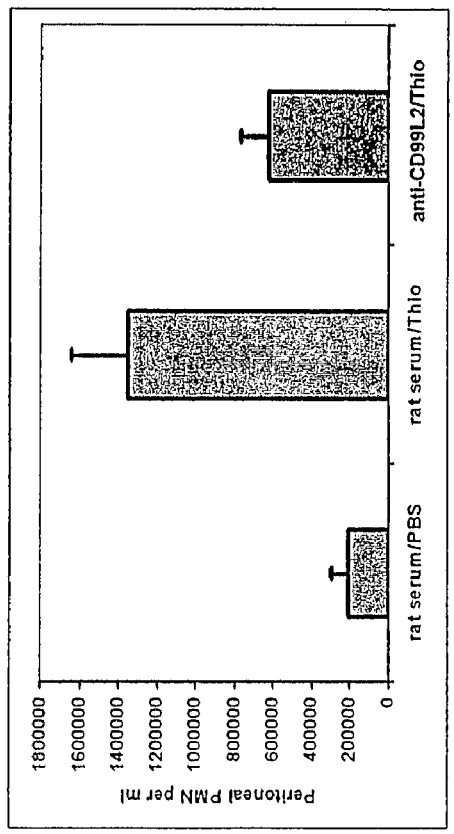
A
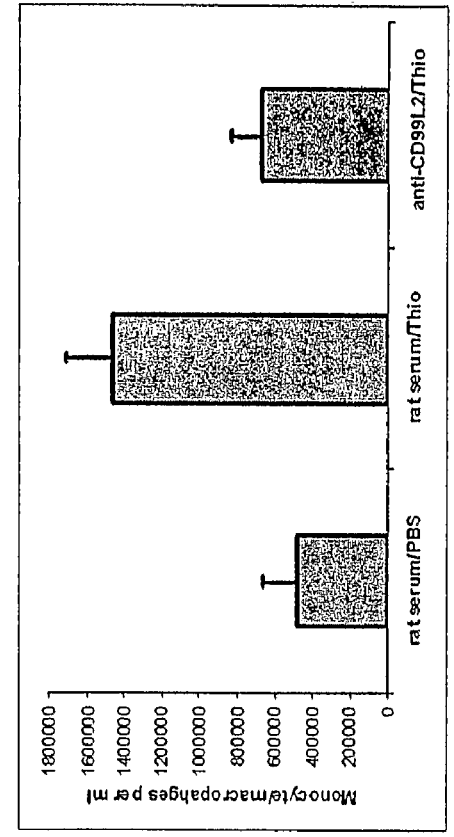
B

Fig. 9
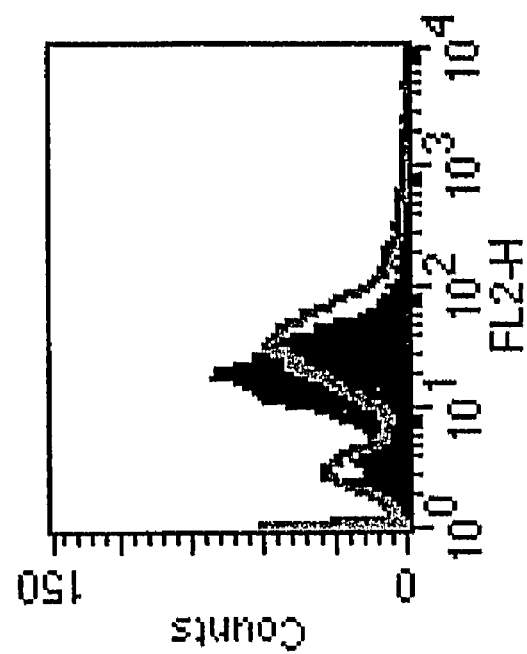
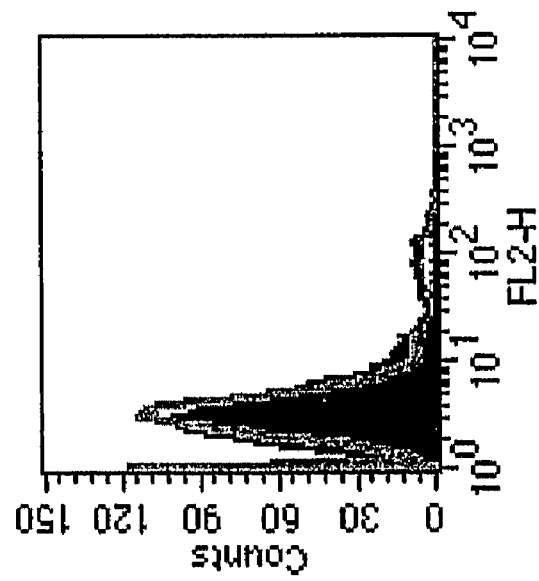

Fig. 10
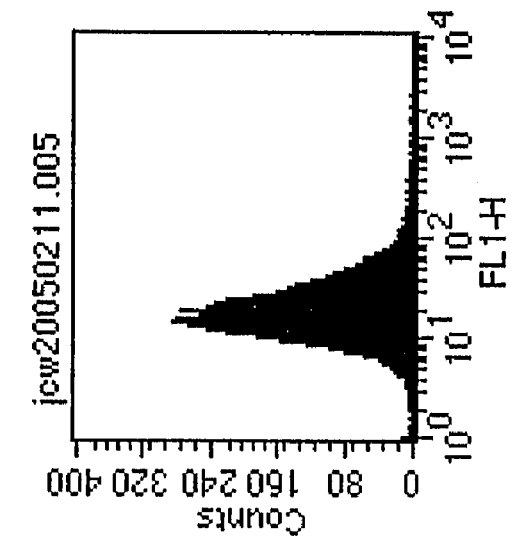
(B) Mu-CD99L2-Transfected Cells
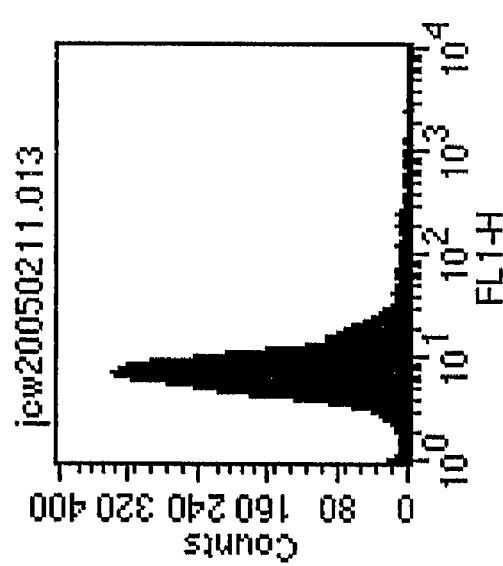
(A) Control Cells

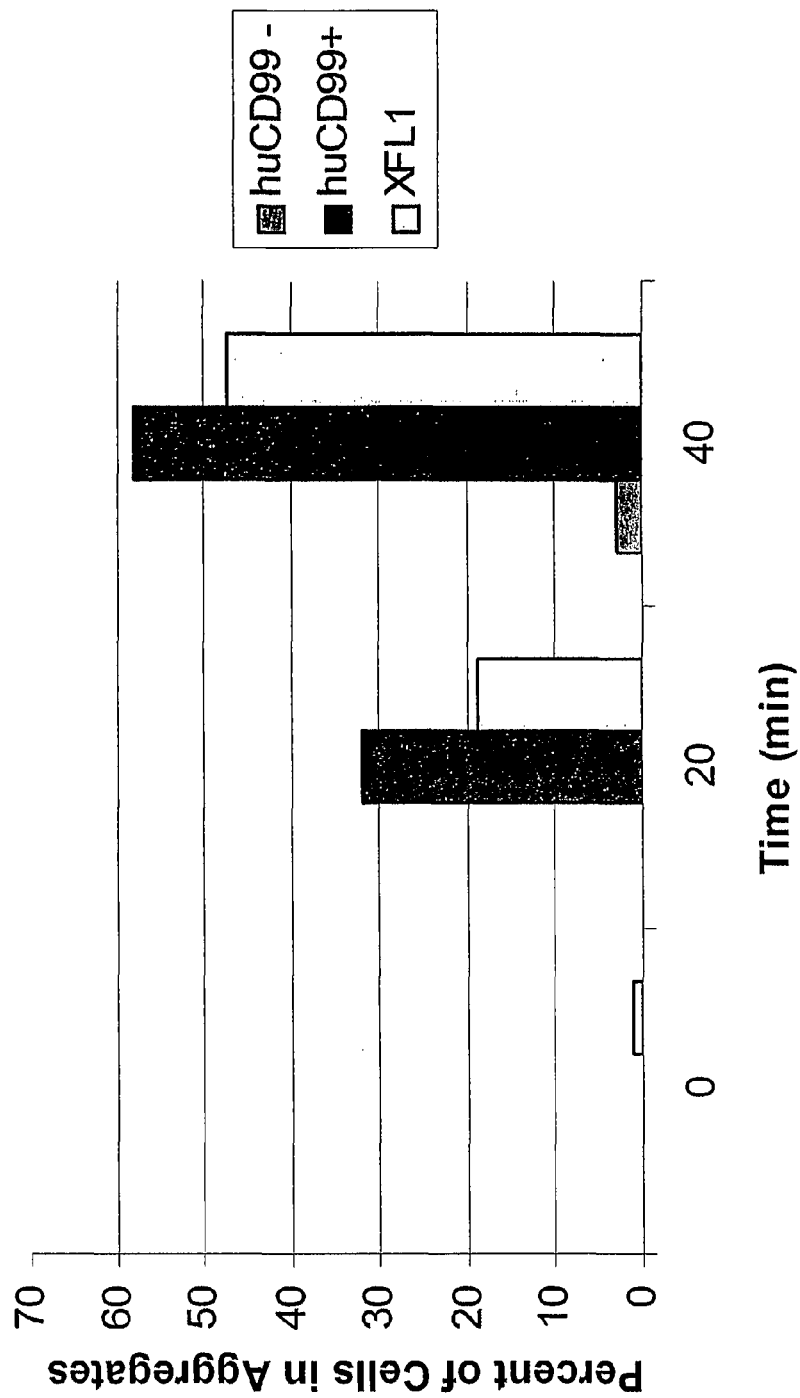

METHODS OF INHIBITING TRANSENDOTHELIAL MIGRATION OF NEUTROPHILS AND MONOCYTES WITH ANTI-CD99L2 ANTIBODIES

CROSS-REFERENCE TO RELATED APPLICATIONS

This application is a 371 national phase of International Application No. PCT/US2006/026084, filed Jun. 30, 2006, which claims the benefit of U.S. Provisional Application No. 60/697,064, filed Jul. 5, 2005. International Application No. PCT/US2006/026084 published in English on Jan. 11, 2007 under Publication No. WO 2007/005898. These applications are hereby incorporated by reference in their entirety.

The research leading to the present invention was supported, in part, by Grant No. HL64774 from the National Institutes of Health. Accordingly, the United States Government may have certain rights in the invention.

FIELD OF THE INVENTION

This invention concerns anti-inflammatory processes, in particular modulating transendothelial migration of leukocytes, and compositions for blocking transendothelial migration of leukocytes.

BACKGROUND OF THE INVENTION

References cited throughout this specification by number are listed at the end of the Examples in the section "REFERENCES".

Previous studies (1-12) have demonstrated a crucial role for platelet/endothelial cell adhesion molecule-1 [PECAM] in transendothelial migration [TEM] of neutrophils [PMN], monocytes [Mo], and natural killer [NK] cells. However, even under the most favorable circumstances, anti-PECAM reagents block only 80-90% of leukocyte influx. While this is as good or better a block of inflammation as has been achieved by targeting a single molecule, the residual 10-20% of leukocytes that are not blocked may represent a clinically significant population under chronic conditions. Furthermore, there are at least some inflammatory models in which PECAM does not appear to play a role.

Leukocyte Migration in Inflammation

Migration of leukocytes into a site of inflammation involves several steps mediated by several families of adhesion molecules. We have focused on the step of transendothelial migration [TEM] because it is the step at which leukocytes become irreversibly committed to entering the inflamed tissues. We have previously described the critical role of PECAM, expressed on the surfaces of all Mo and PMN and concentrated at the borders of endothelial cells, in TEM. Under the best-controlled conditions, anti-PECAM reagents block 80-90% of TEM in in vitro and in many in vivo models. However, there are consistently at least 10-20% of leukocytes that escape this blockade (1, 2, 4, 6, 8). Furthermore, at least one in vivo model has been described in which antibody against PECAM has no effect (9). Targeted deletion of PECAM results in mice with no significant defects in their acute inflammatory response (26). Therefore, mechanisms of TEM independent of PECAM exist. Knowing these mechanisms will lead to a better understanding of inflammation. Targeting these pathways may be a useful adjunct to anti-inflammatory therapies aimed at PECAM.

Molecularly Dissectable Steps in Leukocyte Emigration

The inflammatory response is a double-edged sword. Mobilization of leukocytes to a focus of inflammation is critical for the rapid resolution of infections and restoration of tissue damage resulting from a variety of injuries. On the other hand, most human pathology results from inflammation that is misdirected or prolonged with the result that host tissues are damaged. Common examples include the inflammatory arthropathies, pulmonary fibrosis, and atherosclerosis, which is currently viewed as a chronic inflammatory disease of the arterial wall (13). Therefore, much attention has been directed toward understanding inflammation at the molecular level in the hopes of being able to better regulate it.

The process of leukocyte emigration has been dissected into a series of sequential adhesion events in the following working model. We can divide leukocyte emigration into these steps because we have reagents that can block each one of these steps.

Rolling. In the first step, some of the leukocytes entering a postcapillary venule in an area of inflammation leave the circulatory stream and adhere loosely, tentatively, and reversibly to the endothelial cell surfaces in a process aptly named "rolling." The selection family of adhesion molecules and their sialylated-Lewis$^x$-decorated ligands appear to be primarily responsible for this initial interaction [reviewed in (14, 15)]. Rolling leukocytes come into direct contact with the endothelium, exposing them to a variety of signals capable of promoting the next step—activating the leukocyte-specific integrins. The binding of leukocytes to E-selectin itself may be a sufficient signal (16). Alternatively or additionally, the leukocytes tethered by selectins are now in a position to be activated by platelet activating factor (17) or other lipid modulators (18), chemokines bound to endothelial surface glycosaminoglycans (19), soluble chemoattractants (20), or ligands that cross-link leukocyte CD31 (3, 21, 22).

Adhesion. Upon activation of their integrins to the high affinity binding state, leukocytes cease rolling and adhere tightly to the endothelial surface. For monocytes and lymphocytes, which express integrins of the both β1 and β2 families, engagement by either integrin may suffice to promote attachment for subsequent transmigration (23). The identified counter-receptors for β1 and β2 integrin-mediated adhesion include ICAM-1, ICAM-2, and VCAM-1, members of the immunoglobulin gene superfamily. Leukocytes bound tightly to the luminal surface of the endothelial cell crawl rapidly to an intercellular junction, a process that requires successive cycles of adhesion and dis-adhesion, as the leukocytes attach at their forward ends and release at their rear.

Transmigration. Upon reaching the junction, leukocytes insert pseudopods between tightly apposed endothelial cells and crawl through, in ameboid fashion, while retaining tight contacts with the endothelial cell. This step is referred to as diapedesis, transendothelial migration [TEM], or transmigration. Platelet/endothelial cell adhesion molecule-1 [PECAM, also known as CD31], a CAM of the immunoglobulin superfamily (24), expressed on the surfaces of leukocytes and platelets and concentrated in the borders between endothelial cells, is involved in this step. Contact between leukocyte PECAM and endothelial PECAM is crucial for the transmigration of the vast majority of neutrophils and monocytes in vitro (1) and in vitro (2, 8). TEM can be inhibited in vitro and in vivo by administering agents that interfere with the homophilic interaction of leukocyte PECAM with endothelial PECAM. These include mAb that bind to PECAM domain 1 and/or 2 and block this critical site, or soluble recombinant PECAM-IgG chimeras containing at least domain 1, which competitively inhibit this interaction (4, 6, 25). Therefore, PECAM-dependent transmigration is a promising target for anti-inflammatory therapy.

Despite advances in understanding of the molecules and mechanisms of leukocyte rolling and adhesion to the apical surface of endothelium (15; 46; 47), there remain significant gaps in the present knowledge of transendothelial migration. PECAM clearly plays an important role in TEM for most PMN and monocytes under most inflammatory conditions studied to date. The function of PECAM in mediating transmigration without affecting apical adhesion defines TEM as a separate step in leukocyte emigration. However, while PECAM is the only molecule that has been identified to play a unique role in TEM, it is clearly not the only molecule involved in TEM.

CD99

CD99 is a 32 kD, highly O-glycosylated molecule that is expressed on the surfaces of most leukocytes and is concentrated at the borders between confluent endothelial cells (Schenkel, A. R. et al., 2002, Nat Immunol 3:143-150). Until recently CD99 belonged to no known gene family (Aubrit, F. et al., 1989, Eur J Immunol 19:1431-1436; Gelin; C. et al, 1989, EMBO J. 8:3253-3259). However, with the cloning of the human and murine genomes, a single related protein, CD99L2, was predicted (Suh, Y. H. et al., 2003, Gene 307: 63-76). CD99 has been described as a co-stimulatory molecule on T cells and thymocytes, but its role in transendothelial migration has only recently been appreciated (Schenkel et al.). Similar to PECAM-1 (CD31), CD99 functions in a homophilic manner in transmigration. Blockade of CD99 on either leukocytes or endothelial cells blocks diapedesis of monocytes as well as does blockade of CD99 on both cell types simultaneously. The same holds true for diapedesis of neutrophils. Fab fragments of anti-CD99 monoclonal antibody blocked diapedesis by over 90% in an in vitro model of transendothelial migration (Schenkel et al.). CD99 controls a step in diapedesis that is different from the step controlled by PECAM-1. Blocking both CD99 and PECAM-1 give an additive effect, essentially abolishing diapedesis completely (Schenkel et al.). The CD99-dependent step is distal to the one controlled by PECAM-1. Leukocytes blocked at the CD99-dependent step are arrested partway across the endothelial junction. The leading edge of the leukocyte is below the endothelial cell, but a major portion of the cell is still in the junction, and the trailing edge remains on the apical surface of the monolayer. This demonstrates that diapedesis is controlled by at least two separate sets of homophilic interactions acting at two separate steps.

SUMMARY OF THE INVENTION

The present invention provides a method of modulating transendothelial migration (TEM) of leukocytes, which method comprises inhibiting CD99L2-mediated leukocyte transmigration through endothelium. In one embodiment of this method, the CD99L2 is located on endothelial cells. In another embodiment, the CD99L2 is located on the leukocytes. In a further embodiment, TEM occurs between activated endothelial cells. In an additional embodiment, the activated endothelial cells are activated as a result of contact with a pro-inflammatory cytokine selected from the group consisting of tumor necrosis factor (TNF) and interleukin-1 (IL-1). In another embodiment, the endothelial cells are found on excised endothelial tissue maintained in a tissue culture.

In a specific embodiment of this method, the endothelial cells are cultured on a permeable membrane in vitro. In one aspect of this embodiment, the endothelial cells are human umbilical vein endothelial cells (HUVEC). In another embodiment, the TEM occurs across endothelial cells in a tissue selected from the group consisting of arterial endothelium, venous endothelium, venular endothelium, and post-capillary venular endothelium. In yet another embodiment, TEM occurs into a site of inflammation.

The invention further provides a method for inhibiting CD99L2-mediated transmigration of leukocytes which comprises contacting the leukocytes, the endothelium, or both with an inhibitor of CD99L2 binding. In one embodiment of this method, the inhibitor of CD99L2 binding is an anti-CD99L2 antibody molecule. In another embodiment, the anti-CD99L2 antibody molecule has the binding specificity of a monoclonal antibody to CD99L2. In a further embodiment, the inhibitor of CD99L2 binding is a soluble CD99L2 molecule or fragments thereof.

The invention also provides a method of treating an inflammatory condition in vitro, which method comprises inhibiting CD99L2-mediated leukocyte transendothelial migration (TEM). In one embodiment of this method, the TEM occurs across endothelial cells in a tissue selected from the group consisting of arterial endothelium, venous endothelium, capillary endothelium, venular endothelium, and post-capillary venular endothelium. In another embodiment, the inflammatory condition is an acute inflammatory condition. In yet another embodiment, the inflammatory condition results from an infection. In a further embodiment, the inflammatory condition is a chronic inflammatory condition.

One embodiment of this invention provides a method for inhibiting CD99L2-mediated TEM comprises contacting the leukocytes, the endothelium, or both with an inhibitor of CD99L2 binding. In one aspect of this embodiment, the inhibitor of CD99L2 binding is an anti-CD99L2 antibody molecule. In another aspect, the anti-CD99L2 antibody molecule has the binding specificity of monoclonal antibody CD99L2. In a further aspect, the inhibitor of CD99L' binding is a soluble CD99L2 molecule or fragments thereof.

The invention further provides an anti-CD99L2 monoclonal antibody molecule, wherein the anti-CD99L2 monoclonal antibody inhibits CD99L2-mediated transendothelial migration (TEM) of leukocytes. In one embodiment of this invention, the monoclonal antibody molecule binds CD99L2 on monocytes, platelets, and granulocytes or endothelial cells. In another embodiment, the monoclonal antibody molecule has the binding characteristics of monoclonal antibody CD99L2. In a preferred embodiment, the monoclonal antibody molecule is a humanized monoclonal antibody.

The invention also provides a method of screening for compounds that may inhibit CD99L2-mediated TEM of leukocytes, which method comprises identifying compounds that bind CD99L2.

The invention further provides a method of screening for compounds that inhibit CD99L2-mediated TEM of leukocytes, which method comprises identifying a compound that inhibits leukocyte binding to CD99L2. In one embodiment of this method, the compound inhibits leukocyte binding to endothelial cells. In another embodiment, the compound inhibits leukocyte transmigration. In a further embodiment, the leukocytes and endothelial cells are co-cultured in vitro in the presence of the compound under conditions that promote leukocyte transmigration, further comprising detecting extent of transmigration of leukocytes through endothelial cells. In yet another embodiment, the compound binds to CD99L2.

BRIEF DESCRIPTION OF THE DRAWINGS

FIG. 1. cDNA sequence of muCD99L2 (SEQ ID NO: 1).

FIG. 2. Predicted amino acid sequence of muCD99L2 (SEQ ID NO: 2) aligned against human CD99 (SEQ ID NO: 3) by the MAXHOM homology algorithm showing substantial homology and identity between the two molecules. Key: h=hydrophobic, l=aliphatic, t=turnlike, a=aromatic, s=small, u=tiny, p=polar, +=positive charge, −=negative charge, o=alcohol, c=charged. (Source of software: Expasy.org website).

FIGS. 3A and 3B. Murine CD99L2 is specifically recognized by rabbit antiserum. (A) Preimmune sera showed background levels of nonspecific staining. (B) Serum from a rabbit immunized with purified muCD99L2 stains COS cells transfected with muCD99L2, which preferentially express the molecule at their borders similar to cells transfected with human CD99. Both sera were diluted 1:100 and detected with Alexa 488-labeled goat anti-rabbit IgG.

FIGS. 7A and 7B. Anti-muCD99L2 blocks acute inflammation in vivo. 100 μl of rat anti-muCD99L2 (anti-CD99L2) or normal rat serum (rat serum) were injected i.v. one hour prior to i.p. injection of thioglycollate broth (Trio) or phosphate buffered saline (PBS) as a control. Leukocytes were harvested by peritoneal lavage 18 hours later. (A) Anti-muCD99L2 leads to reduced levels of PMNs. (B) Anti-muCD99L2 leads to reduced levels of monocytes/macrophages.

FIG. 9A-9B. mAb 9G5 binds to muCD99L2-transfected COS cells. Two lines of COS cells transfected with muCD99L2-FLAG were nonenzymatically resuspended and incubated with mAb hybridoma supernates for 30 min on ice, then washed and incubated in AlexaFluor488-labeled goat anti-rat IgG for 30 min. on ice, washed and analyzed by flow cytometry. (A) 4F2 is a typical negative hybridoma. The same staining was seen with normal rat serum. (B) 9G5 specifically stains muCD99L2-transfected cells, since it did not react with untransfected COS cells (not shown).

FIG. 10A-10B. mAb 9G5 reacts selectively with muCD99L2-transfected L cells, Dilute culture supernates of mAb 9G5 (1:100 dilution) were reacted with (A) control cells (line D6) or (B) muCD99L2-transfected L cells (line XFL1) as in FIG. 9, detected with fluorescent secondary anti-rat IgG. (More intense staining was seen with more concentrated supernate on the transfected cells, but not on the control cells.)

FIGS. 12A and 12B. Expression of muCD99L2 imparts on L cell fibroblasts the ability to adhere to each other. Two independent experiments were performed with two independent lines of L cells transfected with muCD99L2. In (A) the line XFL8 was studied. In (B) line XFL1 was studied. In both cases aggregation was time dependent, as previously found (Muller et al., 1992, J. Exp. Med. 175:1401-1404; Schenkel et al., 2002, Nature Immunol. 3:143-150). In (A) L cell line D6 served as the negative control. These cells represent the parental L cell line transfected with the same plasmid as the others but expressing human PECAM in the inverted orientation. The positive controls were #6 cells expressing human PECAM and #1 cells expressing human CD99. In (B) the positive control was again #1 cells expressing human CD99 aggregating in the presence (+) of divalent cations. The negative control was the same cell line incubating in the absence (−) of divalent cations (Schenkel et al. 2002, Nature Immunol. 3:143-150).

DETAILED DESCRIPTION

Previous studies on PECAM-1 and CD99 suggested the existence of other molecules expressed on both leukocytes and endothelial cells and capable of homophilic interaction could be involved in transendothelial migration. The inventors have discovered that CD99L2 is just such a molecule. While the predicted structure of murine and human CD99L2 has been published (Suh et al.), the function of this molecule was not speculated upon. Based on the independent cDNA cloning of murine CD99L2 (muCD99L2) and studies of its actions in vitro and in vivo, the inventors have discovered that muCD99L2 has a role in diapedesis, and that blockade of muCD99L2 inhibits inflammation. Based on the inventors' studies and the close homology to human CD99L2, it is apparent that human CD99L2 has important functions in inflammation, and blocking the function of CD99L2 will be a useful anti-inflammatory strategy.

The present application is based, in part, on identification of a 45 kD membrane protein expressed at the borders between confluent endothelial cells as well as on the surfaces of leukocytes. This protein has been identified as murine CD99L2. In an in vivo assay, a polyclonal antibody against this molecule selectively blocks migration of monocytes and neutrophils into a site of inflammation. It is quite possible that the most important physiologic function(s) of muCD99L2, and by inference the homologous human CD99L2, may be related to leukocyte transmigration, where mAb against the closely related family member CD99 blocks transmigration by greater than 90% (Schenkel et al.).

The inventors have cloned muCD99L2, a murine CD99 paralogue with regions of high homology to human CD99, and even higher homology to the human version of CD99L2. Human CD99L2 is located on the q arm of the X chromosome (Suh et al.). The cDNA sequence is shown in FIG. 1 and the predicted amino acid sequence and homology with human CD99 are shown in FIG. 2.

Figure 4:
FIG. 4A-4D. Murine CD99L2 is expressed on endothelium in situ. Frozen sections from mouse kidney (A, C) or heart (B, D) were incubated with a 1:1,000 dilution of rat anti-murine CD99L2 serum (A, B) or normal rat serum (C, D) for 30 minutes, washed and incubated with HRP-labeled rabbit anti-rat IgG before developing with diaminobenzidine and hydrogen peroxide. Endothelium of arteries (a) and veins (v) are clearly stained in both kidney and heart (arrows). In addition glomerular (g) and peritubular capillaries are stained in the kidney (panel A) as well as capillaries between myofibers in the heart (B). No significant staining is seen with nonimmunized sera. Bar=200 μm.
Figure 5:
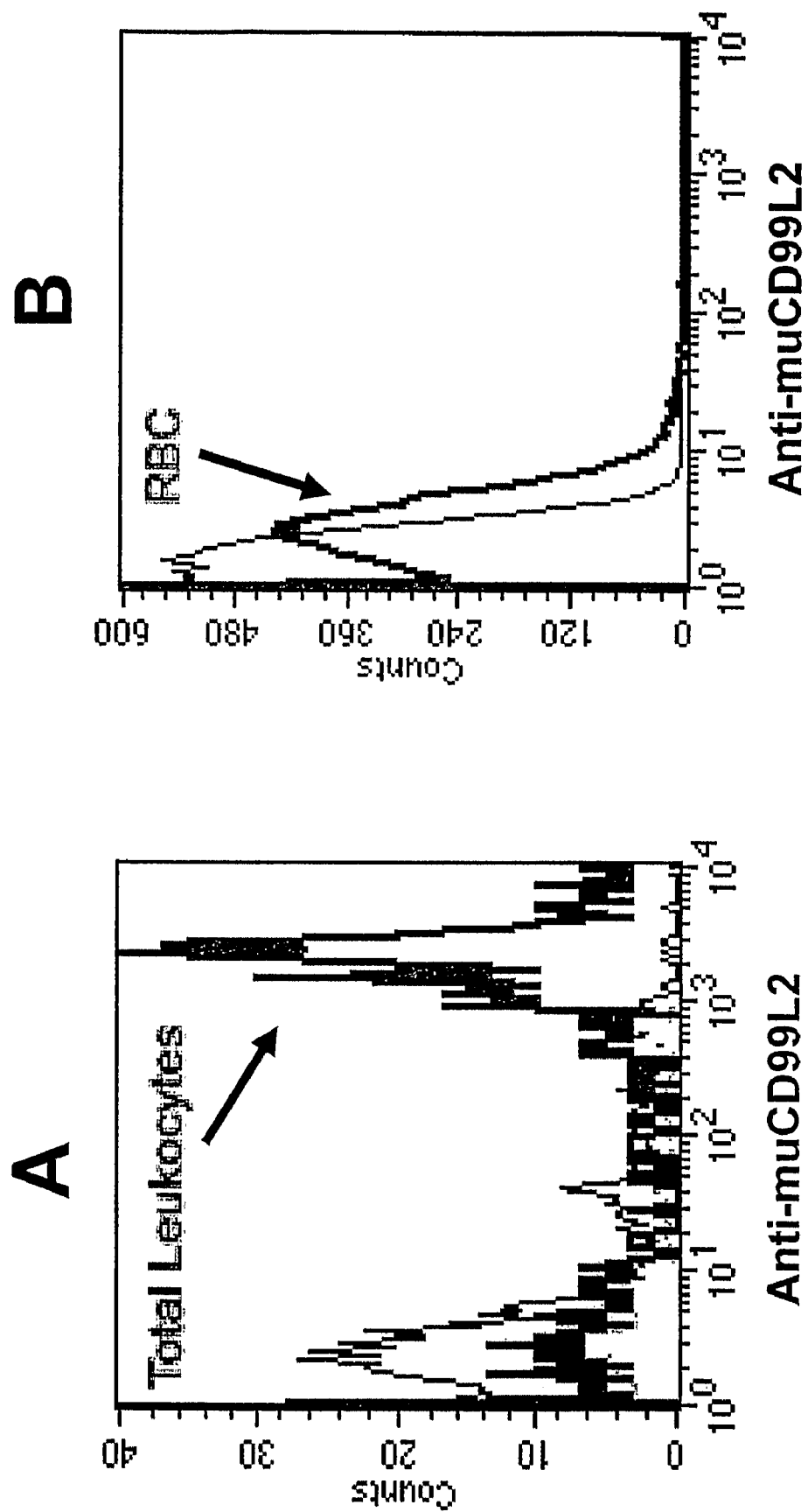
FIGS. 5A and 5B. Expression of muCD99L2 on blood cells. Rat anti-muCD99L2 at a final dilution of 1:1000 was used to stain anti-coagulated mouse blood for flow cytometric analysis. Leukocytes and erythrocytes (RBC) were gated by forward and side-scatter characteristics and results displayed separately. (A) Leukocytes (grey histograms) display intense fluorescence, while the staining of RBC is detectable, but about 1000 fold lower (black histograms). (B) Staining was detected using biotinylated rabbit anti-rat IgG and PE-labeled streptavidin. Black histogram=no primary antibody added.

The Example presented herein demonstrates that polyclonal and monoclonal antibodies generated against muCD99L2 identify muCD99L2 as present on vascular endothelial cells of arteries, veins, and capillaries of many organs (FIGS. 4, 6) as well as on leukocytes (FIG. 5). Functional data demonstrate that CD99L2 expression in fibroblasts imparts on them the ability to adhere to each other (FIG. 12). This implies that CD99L2 on leukocytes mediate adhesive interactions with CD99L2 on endothelial cells, in a similar manner to the manner in which the related, but distinct, molecule CD99 does (Schenkel et al.). More important, two different polyclonal anti-CD99L2 antibodies (one developed in rabbit, one developed in rat) blocked inflammation in an in vivo model of peritonitis (FIG. 7).

Similarities between human CD99 and CD99L2 underline the importance of muCD99L2 studies in developing therapeutics targeted at human CD99L2 for the treatment of inflammation and inflammatory diseases in the human patient population. Like CD99, the muCD99L2 and human CD99L2 sequences encode a type I membrane protein with several potential sites for O-linked glycosylation, but no sites for N-linked glycosylation. Murine CD99L2 is expressed on endothelial cells, monocytes, lymphocytes, granulocytes, and erythrocytes in mice-all cells known to express CD99 in humans. Like human CD99, and by corallary human CD99L2, muCD99L2 is involved in inflammation. Studies on the role of muCD99L2 in inflammation will provide critical insights into the function of human CD99L2.

Murine CD99L2

The inventors haste cloned muCD99L2 (also called CD99L2 or muCD99L2), a murine CD99 paralogue with regions of high homology to CD99. muCD99L2 is also similar to a second CD99-related gene in humans, CD99L2. Human CD99L2 is located on the q arm of the X chromosome.

Despite the advances in knowledge of leukocyte and EC molecules involved in leukocyte emigration, the mechanisms that regulate diapedesis are still unknown. PECAM and CD99 are constitutively expressed (Schenkel, et al., 2002, Nature Immunol. 3:143-150). Thus, understanding how molecules regulating diapedesis function should facilitate the development of better and more selective anti-inflammatory therapies. The PECAM-containing surface-connected compartment (SCC) is a novel organelle in endothelia. It is significant because its role in diapedesis demonstrates that EC are actively involved in promoting diapedesis, not just by the expression of the appropriate adhesion molecules for leukocytes to recognize, but in the physical movement of leukocytes across the vascular intima (Mamdouh, et al., 2003, Nature 421:748-753). PECAM and CD99 have sequential, non-overlapping functions in diapedesis (Schenkel, et al., 2002, Nature Immunol. 3:143-150). However, CD99 has no known signaling motifs and is a member of a very small and unique molecular family unlike any other leukocyte-endothelial cell adhesion molecule. Thus, there are no hints from its structure as to how it functions.

The murine form of CD99L2, alternately referred to as muCD99L2, has been identified. It is critical to know whether murine CD99L2 plays a similar role in leukocyte emigration in vivo as it does in vitro. This is especially important because murine CD99L2 appears to be more similar to human CD99L2 than it is to human CD99. It is possible that the roles of human CD99 in inflammation emerged after the gene evolved from the common ancestral progenitor that gave rise to murine CD99. muCD99L2 is expressed on all murine cell types tested thus far whose human counterparts express CD99, Antibodies against muCD99L2 block recruitment of both PMN and monocytes to areas of acute inflammation in vivo. The studies presented herein examine the role of muCD99L2 in several models of acute inflammation.

The similarities between human CD99 and muCD99L2 underline the importance of muCD99L2 studies in developing CD99-targeted therapeutics for treatment of inflammation and inflammatory diseases in the human patient population. Like CD99, the muCD99L2 sequence encodes a type I membrane protein with several potential sites for O-glycosylation but no potential sites for N-glycosylation. muCD99L2 is expressed on monocytes, lymphocytes, granulocytes, and erythrocytes in mice-all cells known to express CD99 in humans. Like human CD99, muCD99L2 is involved in leukocyte migration and inflammatory responsiveness.

Two murine models of acute inflammation in which the effect of blocking mAb can be assessed both quantitatively and qualitatively, can show that the block produced by interfering with CD99-type molecules is at the level of TEM or adhesion. The role of muCD99L2 is evaluated in wild-type mice as well as in mice in which PECAM is maximally blocked, muCD99L2 activity can also be tested in any of three lines of mice in which PECAM is either absent or nonfunctional, and therefore TENS occurs independently of PECAM. PECAM-independent or alternative pathways will be easier to identify in such mice. The effects of blocking antibodies to these new molecules are tested in wild-type mice to determine the effect of blocking these molecules by themselves; Tg8 mice that constitutively express circulating PECAM-IgG and have a maximal block of PECAM function; PECAM deficient [knockout] mice, which have no PECAM; and Tg5 and Tg11 mice that constitutively express supratherapeutic levels of soluble PECAM-1 and are refractory to its effects, despite having normal levels of PECAM on their endothelial cells and leukocytes. These studies provide a better understanding of the CD99L2-mediated mechanisms involved in transendothelial migration of leukocytes and identify additional therapeutic compounds for anti-inflammatory therapy.

As used herein, the term "transendothelial migration" (TEM) refers to the movement of leukocytes from the apical surface to the basal lamina of endothelial cells and beyond. Leukocytes migrate between junctions formed in the endothelium between individual endothelial cells. Generally, TEM occurs when the endothelial cells are activated, e.g., with TNF, IL-1, or other pro-inflammatory mediators. TEM can also occur constitutively, particularly for monocytes and lymphocytes, and will occur at a lower, less robust level across endothelial cells as a consequence of leukocyte adhesion even in the absence of direct activation of the endothelial cells. Thus, TEM occurs in vivo at inflammatory foci; and in vitro, across cultured endothelial cells preferably after activation of the endothelial cells and/or creating a chemotactic gradient. The inventors have found that the in vitro system replicates inflammatory conditions in vivo for studying TEM with a high degree of predictability.

The term "leukocytes" includes, but is not limited to, polymorphonuclear leukocytes (e.g., neutrophils), monocytes (which differentiate into dendritic cells or macrophages after transmigration into a site to which they are attracted), granulocytes (including eosinophils and basophils), natural killer cells and lymphocytes, e.g., T lymphocytes, as well as circulating dendritic cell precursers.

The term "endothelial cell" (or EC) has ordinary meaning in the art. Endothelial cells make up endothelium, which is found inter alia in the lumen of vascular tissue (veins, arteries, and capillaries) throughout the body. The "apical surface" of endothelium is the lumenal surface, i.e., in contact with blood. The basal lamina or basement membrane is the layer of extracellular matrix that separates the endothelium from the wall of the vessel. In most cases of inflammation, leukocytes emigrate across post-capillary venules whose wall consists of a discontinuous layer of vascular smooth muscle cells that separate the vessel from the tissue it is supplying.

Activation of endothelial cells can result from contact with stimulatory mediators. For purposes of the present invention, activation of endothelial cells results from contact with pro-inflammatory cytokines such as, but not limited to, tumor necrosis factor (TNF) and interleukin-1 (IL-1), particularly IL-1β.

The present invention encompasses assessing CD99L2-mediated TEM and compounds that are candidate inhibitors of this process in assays in vitro and in vivo. For the in vitro assays, the endothelial cells are preferably cultured on a permeable membrane or collagen gel. In vivo, TEM occurs at a site of inflammation, which can be induced (e.g., with thioglycollate or croton oil treatment) or result from a natural inflammatory condition (infection, wound, autoimmunity).

An "inhibitor of CD99L2" is a molecule that blocks or reduces binding of CD99L2 to itself or its heterophilic binding partner (i.e., CD99L2 ligand or CD99L2 receptor), i.e., prevents CD99L2 from interacting with (e.g., binding to) the heterophilic or homophilic binding partner and mediating TEM. In a specific embodiment, an anti-CD99L2 monoclonal antibody molecule is such an inhibitor. Alternatively, an extracellular fragment of CD99L2 is an inhibitor, and more particularly, a competitive inhibitor. An "extracellular fragment of CD99L2" can be the entire extracellular domain, i.e., from the N-terminus to about the start of the transmembrane domain, or a smaller portion thereof comprising an interaction domain of CD99L' with its binding partner (including chimeric constricts of the CD99L2 extracellular domain, e.g., with an Fc domain of an immunoglobulin molecule); a carbohydrate, particularly an O-linked carbohydrate; or a lectin ligand. Thus, suitable inhibitors can interact with CD99L2 carbohydrates; such inhibitors can be various lectins. Alternatively, soluble carbohydrates or carbohydrate mimetics can be used to block the lectin that interacts with critical carbohydrates on CD99L2. Similarly, peptides or peptidomimetics can block interaction with a polypeptide interaction domain of CD99L2. Furthermore, combinations of the foregoing can, under certain circumstances, prove most effective at inhibiting CD99L2. In a specific embodiment, such an inhibitor is an anti-CD99L2 antibody molecule, more specifically, an anti-CD99L2 monoclonal antibody molecule.

The term anti-CD99L2 antibody molecule includes immunoglobins that recognize CD99L2 homologues of mice, human beings or other species, derivatives of such antibodies with at least the ligand binding portion of the CD99L2 homologues mentioned, may be used as well, including, but not limited to, single chain, Fv, Fab, Fab', F[ab']$_2$, chimeric antibodies, humanized antibodies and the like.

The term "inflammatory condition" refers to either an acute or chronic inflammatory condition, which can result from infections or non-infectious causes. Various infectious conditions include meningitis, encephalitis, uveitis, colitis, dermatitis, and adult respiratory distress syndrome. Non-infectious causes include trauma (burns, cuts, contusions, crush injuries), autoimmune diseases, and organ rejection episodes. Thus, in specific embodiments, an inflammatory condition results from a condition selected from the group that includes: atherosclerosis (arteriosclerosis); autoimmune conditions, such as multiple sclerosis, systemic lupus erythematosus, polymyalgia rheumatica (PMR), rheumatoid arthritis and other forms of inflammatory arthritis, Sjogren's Syndrome, progressive systemic sclerosis (scleroderma), ankylosing spondylitis, polymyositis, dermatomyositis, pemphigus, pemphigoid, Type I diabetes mellitus, myasthenia gravis, Hashimoto's thyroditis, Graves' disease, Goodpasture's disease, mixed connective tissue disease, sclerosing cholangitis, inflammatory bowel disease including Crohn's Disease (regional enteritis) and ulcerative colitis, pernicious anemia, inflammatory dermatoses; usual interstitial pneumonitis (UIP), asbestosis, silicosis, berylliosis, talcosis, the various forms all forms of pneumoconiosis, sarcoidosis (in the lung and in any other organ), desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa); inflammatory dermatoses not presumed to be autoimmune; chronic active hepatitis; delayed-type hypersensitivity reactions (e.g., poison ivy dermatitis); pneumonia or other respiratory tract inflammation due to any cause; Adult Respiratory Distress Syndrome (ARDS) from any etiology; encephalitis, with inflammatory edema; immediate hypersensitivity reactions including, but not limited to, asthma, hayfever, cutaneous allergies, acute anaphylaxis; diseases involving acute deposition of immune complexes, including, but not limited to, rheumatic fever, acute and/or chronic glomerulonephritis due to any etiology, including specifically post-infectious (e.g., post-Streptococcal) glomerulonephritis, acute exacerbations of Systemic Lupus Erythematosus; pyelonephritis; cellulitis; cystitis; acute cholecystitis; and conditions producing transient ischemia anywhere along the gastrointestinal tract, bladder, heart, or other organ, especially those prone to rupture; sequelae of organ transplantation or tissue allograft, including allograft rejection in the acute time period following allogeneic organ or tissue transplantation and chronic host-versus-graft rejection.

The phrase "pharmaceutically acceptable", whether used in connection with the pharmaceutical compositions of the invention or vaccine compositions of the invention, refers to molecular entities and compositions that are physiologically tolerable and do not typically produce untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin ($18^{th}$ edition)

The term "about" or "approximately" will be known to those skilled in the art in light of this disclosure. Preferably, the term means within 20%, more preferably within 10%, and more preferably still within 5% of a given value or range. Alternatively, especially in biological systems, the term "about" preferably means within about a log (i.e., an order of magnitude) preferably within a factor of two of a given value, depending on how quantitative the measurement.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins, and may or may not include regulatory DNA sequences, such as promoter sequences, that determine for example the conditions under which the gene is expressed. The transcribed region of a gene can include 5'- and 3'-untranslated regions (UTRs) and introns in addition to the translated (coding) region.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of or "operably associated with" transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as an mRNA or a protein. The expression product itself, e.g. the resulting RNA or protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell. "Conditions that permit expression", in vitro are culture conditions of temperature (generally about 37° C.), humidity (humid atmosphere), carbon dioxide concentration to maintain pH (generally about 5% $CO_2$ to about 15% $CO_2$), pH (generally about 7.0 to 8.0, preferably 7.5), and culture fluid components, that depend on host cell type. In vivo, the conditions that permit expression are primarily the health of the non-human transgenic animal, which depends on adequate nutrition, water, habitation, and environmental conditions (light-dark cycle, temperature, humidity, noise level). In either system, expression may depend on a repressor or inducer control system, as well known in the art.

The term "transfection" means the introduction of a "foreign" (i.e. extrinsic or extracellular) gene, DNA or RNA sequence into a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as stall, stop, promoter, signal, secretion, or other sequences used by a cell's genetic machinery. The gene or sequence may include nonfunctional sequences or sequences with no known function. A host cell that receives and expresses introduced DNA or RNA has been "transfected" and is a "transfectant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA segment that can be inserted into a vector or into another piece of DNA at a defined restriction site. Preferably, a cassette is an "expression cassette" in which the DNA is a coding sequence or segment of DNA that codes for an expression product that can be inserted into a vector at defined restriction sites. The cassette restriction sites generally are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid" that generally is a self-contained molecule of double-stranded DNA, usually of bacterial origin, that can readily accept additional (foreign) DNA and which can be readily introduced into a suitable host cell. A plasmid vector often contains coding DNA and promoter DNA and has one or more restriction sites suitable for inserting foreign DNA. A large number of vectors, including plasmid and fungal vectors, have been described for replication and/or expression in a variety of eukaryotic and prokaryotic hosts. Non-limiting examples include pKK plasmids (Amersham Pharmacia Biotech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra. The host cell may be found in vitro, i.e., in tissue culture, or in vivo, i.e., in a microbe, plant or animal.

The term "expression system" means a host cell and compatible vector under suitable conditions, e.g., for the expression of a protein coded for by foreign DNA carried by the vector and introduced to the host cell. Common expression systems include *E. coli* host cells and plasmid vectors, insect host cells and Baculovirus vectors, and mammalian host cells and vectors. In a specific embodiment, the protein is expressed in COS-1 or CHO cells. Other suitable cells include NSO cells, HeLa cells, 293T (human kidney cells), mouse primary myoblasts, and NIH 3T3 cells.

The term "heterologous" refers to a combination of elements not naturally occurring. For example, heterologous DNA refers to DNA not naturally located in the cell, or in a chromosomal site of the cell. A heterologous expression regulatory element is such an element operatively associated with a different gene than the one it is operatively associated with in nature. In the context of the present invention, a protein coding sequence is heterologous to the vector DNA in which it is inserted for cloning or expression, and it is heterologous to a host cell containing such a vector, in which it is expressed, e.g., a CHO cell.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization*, B. D. Hames & S. J. Higgins eds. (1985); *Transcription And Translation*, B. D. Hames & S. J. Higgins, eds. (1984); *Animal Cell Culture*, R. I. Freshney, ed. (1986); *Immobilized Cells And Enzymes*, IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994).

Methods of Producing Antibody Molecules

The antibody molecules of this invention can be produced by any method known in the art for the synthesis of immunoglobulins, in particular, by chemical synthesis or by recombinant expression. Such an isolated nucleic acid that contains a nucleotide sequence encoding the antibody molecule can be produced using any method known in the art. Antibody fragments, such as Fab and F[ab']2, may be produced by proteolytic treatment of whole antibodies.

Various procedures known in the art may be used for the production of polyclonal antibodies to CD99L2 or derivative or analog thereof. For the production of antibody, various host animals can be immunized by injection with the CD99L2 polypeptide, or a derivative (e.g., fragment or fusion protein) thereof, including but not limited to rabbits, mice, rats, sheep, goats, etc. In one embodiment, the CD99L2 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the CD99L2-polypeptide, or fragment, analog, or derivative thereof, any technique that provides for the production of antibody molecules by continuous cell lines in culture may be used. These include but are not limited to the hybridoma technique originally developed by Kohler and Milstein (Nature 1975, 256:495-497), as well as the trioma technique, the human B-cell hybridoma technique (Kozbor et al., Immunology Today 1983, 4:72; Cote et al., Proc. Natl. Acad. Sci. USA 1983, 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (PCT Publication No. WO 89/12690). In fact, according to the invention, techniques developed for the production of "chimeric antibodies" (Morrison et al., J. Bacteriol., 1984, 159:870; Neuberger et al., Nature 1984, 312:604-608; Takeda et al., Nature 1985, 314:452-454) by splicing the genes from a mouse antibody molecule specific for an CD99L2 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476, 786, 5,132,405, and 4,946,778) can be adapted to produce CD99L2 polypeptide-specific single chain antibodies. Indeed, these genes can be delivered for expression in vivo. An additional embodiment of the invention utilizes the techniques described for the construction of Fab expression libraries (Huse et al., Science 1989, 246:1275-1281) to allow rapid and easy identification of monoclonal Fab fragments with the desired specificity for a CD99L2 polypeptide, or its derivatives, or analogs.

CD99L2 Polypeptide Expression

Once a nucleic acid containing a nucleotide sequence encoding at least a ligand-binding portion of CD99L2 has been cloned, then the coding sequence can be inserted into a recombinant expression vector. Such engineering of the coding sequence can be accomplished by routine recombinant DNA techniques known in the alt.

The nucleic acid encoding the polypeptide optionally contains a nucleotide sequence encoding a leader sequence that directs the secretion of the protein molecule. In the specific case of CD99L2, which is a transmembrane glycoprotein, a secreted form would be engineered to encode only the extracellular portion, or limited region(s) of the extracellular portion, in order to ensure secretion.

The expression vector can then be transferred to a host cell in vitro or in vivo by conventional techniques and the transfected cells can be cultured by conventional techniques to produce CD99L2. For example, by transient transfection of the expression vector encoding CD99L2 into COS cells, culturing the cells for an appropriate period of time to permit expression, and then taking the supernatant from the COS cells, which supernatant contains the secreted, expressed CD99L2.

The host cells used to express CD99L2 may be either bacterial cells such as *Escherichia coli* or eukaryotic cells. In particular, mammalian cells such as Chinese hamster oval, cells (CHO) or COS cells, used in conjunction with a vector in which expression of CD99L2 is under control of the major intermediate early gene promoter element from human cytomegalovirus is an effective expression system.

A variety of host-expression vector systems may be utilized to express CD99L2. Such host-expression systems represent vehicles by which the coding sequences of interest may be produced and subsequently purified, but also produce cells which may, when transformed or transfected with the appropriate nucleotide coding sequences, exhibit CD99L2 in situ. These systems include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing CD99L2 coding sequences; insect cell systems infected with recombinant virus expression vectors (e.g., baculovirus) containing the CD99L2 coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing CD99L2 coding sequences; mammalian cell systems (e.g., COS, CHO, BHK, 293, and 3T3 cells) harboring recombinant expression constructs containing promoters derived from the genome of mammalian cells (e.g., the metallothionein promoter) or from mammalian viruses (e.g., the adenovirus late promoter; the vaccinia virus 7.5K promoter).

Expression of the protein or polypeptide may be controlled by any promoter/enhancer element known in the art, but these regulatory elements must be functional in the host selected for expression. Promoters that may be used to control gene expression include, but are not limited to, cytomegalovirus (CMV) promoter (U.S. Pat. Nos. 5,385,839 and 5,168,062), the SV40 early promoter region (Benoist and Chambon, Nature 1981, 290:304-310), the promoter contained in the 3' long terminal repeat of Rous sarcoma virus (Yamamoto, et al., Cell 1980, 22:787-797), the herpes thymidine kinase promoter (Wagner et al., Proc. Natl. Acad. Sci. USA, 1981, 78:1441-1445), the regulatory sequences of the metallothionein gene (Brinster et al., Nature 1982, 296:39-42); prokaryotic expression vectors such as the β-lactamase promoter (Villa-Komaroff, et al., Proc. Natl. Acad. Sci. USA, 1978, 75:3727-3731), or the tac promoter (DeBoer, et al., Proc. Natl. Acad. Sci. USA, 1983, 80:21-25); see also "Useful proteins from recombinant bacteria" in Scientific American 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 1985, 315:338-340; Kollias et al., Cell 1986, 46:89-94), hematopoietic stem cell differentiation factor promoters, erythropoietin receptor promoter (Maouche et al., Blood 1991, 15:2557), etc.

In bacterial systems, a number of expression vectors may be advantageously selected depending upon the use intended for the CD99L2 being expressed. For example, when a large quantity of such a protein is to be produced, for the generation of pharmaceutical compositions of CD99L2, vectors which direct the expression of high levels of fusion protein products that are readily purified may be desirable. Such vectors include, but are not limited to, the *E. coli* expression vector pUR-278 (Ruther et al., EMBO J. 1983, 2:1791), in which the CD99L2 coding sequence may be ligated individually into the vector in frame with the lac Z coding region so that a fusion protein is produced; pIN vectors (Inouye & Inouye, Nucleic Acids Res. 1985, 13:3101-3109; Van Hleeke & Schuster, J. Biol. Chem. 1989, 264:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The CD99L2 coding sequence may be cloned individually into non-essential regions (for example, the polyhedrin gene) of the virus and placed under control of an AcNPV promoter (for example, the polyhedrin promoter).

In mammalian host cells, a number of viral-based and non-viral-based expression systems may be utilized. In cases where an adenovirus is used as an expression to vector, the CD99L2 coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody in infected hosts (see, e.g., Logan & Shenk, Proc. Natl. Acad. Sci. USA, 1984, 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et. al., Methods in Enzymol. 1987, 153:516-544).

Additionally, a host cell strain may be chosen that modulates the expression of the inserted sequences, or modifies and processes the gene product in the specific fashion desired. Different host cells have characteristics and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38.

For long-term, high-yield production of recombinant proteins, stable expression is preferred. For example, cell lines that stably express CD99L2 may be engineered. Rather than using expression vectors that contain viral origins of replication, host cells can be transformed with DNA controlled by appropriate expression control elements (e.g., promoter, enhancer sequences, transcription terminators, polyadenylation sites, etc.) and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in thin can be cloned and expanded into cell lines. This method may advantageously be used to engineer cell lines that express the antibody. Such engineered cell lines may be particularly useful in screening and evaluation of compounds that interact directly or indirectly with the antibody.

A number of selection systems may be used, including but not limited to the herpes simplex virus thyrmidine kinase (Wigler et al., Cell 1977, 11:223), hypoxanthine-guanine phosphoribosyltransferase (Szybalska & Szybalski, Proc. Natl. Acad. Sci. USA 1962, 48:2026), and adenine phosphoribosyltransferase (Lowy et al., Cell 1980, 22:817) genes can be employed in tk-, hgprt-, or aprt-cells, respectively. Also, antimetabolite resistance can be used as the basis of selection for the following genes: dhfr, which confers resistance to methotrexate (Wigler et al., Proc. Natl. Acad. Sci. USA 1980, 77:3567; O'Hare et al., Proc. Natl. Acad. Sci. USA 1981, 78:1527); gpt, which confers resistance to mycophenolic acid (Mulligan & Berg, Proc. Natl. Acad. Sci. USA 1981, 78:2072); neo, which confers resistance to the aminoglycoside G-418 (Colberre-Garapin et al., J. Mol. Biol. 1981, 150: 1); and hygro, which confers resistance to hygromycin (Santerre et al., Gene 1984, 30:147).

The expression levels of CD99L2 can be increased by vector amplification (for a review, see Bebbington and Hentschel, The Use of Vectors Based on Gene Ampliflication for the Expression of Cloned Genes in Mammalian Cells in DNA Cloning, Vol. 3, Academic Press, New York, 1987). When a marker in the vector system expressing CD99L2 is amplifiable, increases in the level of inhibitor present in the culture medium of the host cell will increase the number of copies of the marker gene. Since the amplified region is associated with the CD99L2 gene, production of the protein will also increase (Crouse et al., Mol. Cell. Biol. 1983, 3:257).

Viral and Non-Viral Vectors

Useful vectors in vitro and in vivo are viral vectors, such as lentiviruses, retroviruses, herpes viruses, adenoviruses, adeno-associated viruses, vaccinia virus, alphavirus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be affected by targeting the transgenic vector to specific cells, such as with a viral vector or a receptor ligand, or by using a tissue-specific promoter, or both. Targeted gene delivery is described in PCT Publication No. WO 95/28494.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques 1992, 7:980-990). Preferably, the viral vectors are replication-defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 1991, 2:320-330), defective herpes virus vector lacking a glycoprotein L gene, or other defective herpes virus vectors (PCT Publication Nos. WO 94/21807 and WO 92/05263); an attenuated adenovirus vector, such as the vector described by Stratford-Perricaudet et al. (J. Clin. Invest. 1992, 90:626-630; see also La Salle et al., Science 1993, 259:988-990); a defective adeno-associated virus vector (Samulski et al., J. Virol. 1987, 61:3096-3101; Samulski et al., J. Virol. 1989, 63:3822-3828; Lebkowski et al., Mol. Cell. Biol., 1988, 8:3988-3996); and a Sindbis virus (a type of alphavirus) (PCT Publication No. WO 98/06237; U.S. Pat. No. 5,091,309).

Various companies produce viral vectors commercially, including, but not limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. USA, 1987, 84:7413-7417; Felgner and Ringold, Science 1989, 337:387-388; see Mackey, et al., Proc. Natl. Acad. Sci. USA, 1988, 85:8027-8031; Ulmer et al., Science 1993, 259:1745-1748). Useful lipid compounds and compositions for transfer of nucleic acids are described in PCT Patent Publication Nos. WO 95/18863 and WO 96/17823, and in U.S. Pat. No. 5,459,127. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo such as a cationic oligopeptide (e.g., PCT Patent Publication No. WO 95/21931), peptides derived from DNA binding proteins (e.g. PCT Patent Publication No. WO 96/25508), or a cationic polymer (e.g., PCT Patent Publication No. WO 95/21931).

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem. 1992, 267:963-967; Wu and Wu, J. Biol. Chem. 1988, 263:14621-14624: Canadian Patent Application No. 2,012,311; Williams et al., Proc. Natl. Acad. Sci. USA 1991, 88:2726-2730). Receptor-mediated DNA delivery approaches can also be used (Curiel et al., Hum. Gene Ther. 1992, 3:147-154; Wu and Wu, J. Biol. Chem. 1987, 262: 4429-4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., C.P. Acad. Sci. 1988, 321:893; PCT Publication Nos. WO 99/01157; WO 99/01158; WO 99/01175).

Therapeutic Use of CD99L2 Inhibitors

The invention also provides methods for treating or preventing diseases and disorders associated with CD99L2-dependent transendothelial migration, e.g., any one or more of the inflammatory conditions disclosed above, by administration of a therapeutic of the invention. Such therapeutics include the aforementioned antibody molecules, small molecules, oligopeptides, proteins, including soluble non-membrane bound CD99L2, and combinations thereof.

Generally, administration of products of a species origin or species reactivity that is the same species as that of the subject is preferred. Thus, in administration to humans, the therapeutic methods of the invention use an antibody molecule that is preferably derived from a human antibody but may be an antibody from a heterologous species such as, for example, a mouse, which may or may not be humanized To enhance the efficacy of the therapeutics contained in the invention, these treatments may be administered in conjunction with other therapies which block the function of other molecules involved in the transendothelial migration of leukocytes. Molecules, other than CD99L2, involved in leukocyte transendothelial migration, may include PECAM.

The subjects to which the present invention is applicable may be any mammalian or vertebrate species, which include, but are not limited to, cows, horses, sheep, pigs, fowl (e.g., chickens, goats, cats, dogs, hamsters, mice, rats, monkeys, rabbits, chimpanzees, and humans. In a preferred embodiment, the subject is a human.

Gene Therapy

In a specific embodiment, vectors comprising a sequence encoding a protein, including, but not limited to, an antibody molecule, as described, or CD99L2, are administered to treat or prevent a disease or disorder associated with the function of CD99L2 in the transendothelial migration of leukocytes. In a specific embodiment of this invention, CD99L2 or the above described antibody molecules, are expressed in the blood stream of the patient in a soluble, non-membrane bound form. Soluble CD99L2 or antibody molecules bind to the CD99L2 located in the membranes of leukocytes or endothelial cells, thereby preventing the intercellular binding of these two cell-types and inhibiting CD99L2-mediated leukoctye transendothelial migration.

In this embodiment of the invention, the therapeutic vector encodes a sequence that produces, extracellularly (with a leader sequence), a protein of the invention.

Any of the methods for gene therapy available in the alt can be used according to the present invention. Exemplary methods are described below.

For general reviews of the methods of gene therapy, see, Goldspiel et al., Clinical Pharmacy 1993, 12:488-505; Wu and Wu, Biotherapy 1991, 3:87-95; Tolstoshev, Ann. Rev. Pharmacol. Toxicol. 1993, 32:573-596; Mulligan, Science 1993, 260:926-932; and Morgan and Anderson, Ann. Rev. Biochem. 1993, 62:191-217; May, TIBTECH 1993, 11:155-215). Methods commonly known in the at of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al., (eds.), 1994, Current Protocols in Human Genetics, John Wiley &, Sons, NY. Vectors suitable for gene therapy are described above.

In one aspect, the therapeutic vector comprises a nucleic acid that expresses a protein of the invention in a suitable host. In particular, such a vector has a promoter operationally linked to the coding sequence for the protein. The promoter can be inducible or constitutive and, optionally, tissue-specific. In another embodiment, a nucleic acid molecule is used in which the protein coding sequences and any other desired sequences are flanked by regions that promote homologous recombination at a desired site in the genome, thus providing for intrachromosomal expression of the protein (Koller and Smithies, Proc. Natl. Acad. Sci. USA 1989, 86:8932-8935; Zijlstra et al., Nature 1989, 342:435-438).

Delivery of the vector into a patient may be either direct, in which case the patient is directly exposed to the vector or a delivery complex, or indirect, in which case, cells are first transformed with the vector in vitro then transplanted into the patient. These two approaches are known respectively, as in vivo and ex vivo gene therapy.

In a specific embodiment, the vector is directly administered in vivo where it enters the cells of the organism and mediates expression of the protein. This can be accomplished by any of numerous methods known in the art, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-S-1-64-N-acetylglucosamine polysaccharide; see, U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, J. Biol. Chem. 1987, 62:4429-4432), etc. In another embodiment, a nucleic acid ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188). Alternatively, the nucleic acid can be introduced intracellularly and incorporated within host cell DNA for expression by homologous recombination (Koller and Smithies, Proc. Natl. Acad. Sci. USA 1989, 86:8932-8935; Zijlstra, et al., Nature, 1989, 342:435-438). These methods are in addition to those discussed above in conjunction with "Viral and Non-viral Vectors".

Alternatively, antibody molecules can also be administered, for example, by expressing nucleotide sequences encoding single-chain antibodies within the target cell population by utilizing, for example, techniques such as those described in Marasco et al. Proc. Natl. Acad. Sci. USA, 1993, 90:7889-7893).

The form and amount of therapeutic nucleic acid envisioned for use depends on the type of disease and the severity of the desired effect, patient state, etc., and can be determined by one skilled in the art.

Formulations and Administration

Therapeutic compositions for use in accordance with the present invention can be formulated in any conventional manner using one or more physiologically acceptable carriers or excipients.

Thus, proteins of this invention or nucleic acids encoding them and their physiologically acceptable salts and solvents can be formulated for administration by inhalation (pulmonary) or insufflation (either through the mouth or the nose), by transdermal delivery, or by transmucosal administration, including, but not limited to, oral, buccal, nasal, opthalmic, vaginal, or rectal administration.

For oral administration, the therapeutics can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups, emulsions or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the therapeutics can take the form of tablets or lozenges formulated in conventional manner.

For administration by inhalation, the therapeutics according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The therapeutics can be formulated for parenteral administration (e.g., intravenous, intramuscular, subcutaneous, intradermal) by injection, via, for example, bolus injection or continuous infusion. Formulations for injection can be presented in unit dosage form, e.g., in vials or ampules or in multi-dose containers, with an added preservative. The compositions can take such forms as excipients, suspensions, solutions or emulsions in oily or aqueous vehicles, and can contain formulatory agents such as suspending, stabilizing and/or dispersing agents. Alternatively, the active ingredient can be in dry, lyophilized (i.e. freeze dried) powder form for constitution with a suitable vehicle, e.g., sterile pyrogen-free water or saline, before use.

The therapeutics can also be formulated in rectal compositions such as suppositories or retention enemas, e.g., containing conventional suppository bases such as cocoa butter or other glycerides.

In addition to the formulations described previously, the therapeutics can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Proteins of the invention can be delivered in poly-glycolic acid/lactic acid (PGLA) microspheres (see U.S. Pat. Nos. 5,100,669 and 4,849,222; PCT Publication Nos. WO 95/11010 and WO 93/07861).

The proteins of the invention may be administered as separate compositions or as a single composition with more than one antibody linked by conventional chemical or by molecular biological methods. Additionally, the diagnostic and therapeutic value of the antibodies of the invention may be augmented by their use in combination with radionuclides or with toxins such as ricin or with chemotherapeutic agents such as methotrexate.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water-free concentrate in a sealed container such as an ampule or sachette indicating the quantity of active agent. Where the composition is administered by injection, an ampule of sterile diluent can be provided so that the ingredients may be mixed prior to administration.

The invention also provides a pharmaceutical pack or kit comprising one or more containers filled with one or more of the ingredients of the formulations of the invention. Associated with such container(s) can be a notice in the form prescribed by a governmental agency regulating the manufacture, use or sale of pharmaceuticals or biological products, which notice reflects approval by the agency of manufacture, use or sale for human administration.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Composition comprising a compound of the invention formulated in a compatible pharmaceutical carrier may also be prepared, placed in an appropriate container, and labelled for treatment of an indicated condition.

Many methods may be used to introduce the formulations of the invention; these include but are not limited to oral, intracerebral, intradermal, intramuscular, intraperitoneal, intravenous, subcutaneous, intranasal routes, and via scarification (scratching through the top layers of skin, e.g., using a bifurcated needle) or any other standard routes of administration.

Effective Dose

The compounds and vectors described herein can be administered to a patient at therapeutically effective doses to treat certain diseases or disorders. A therapeutically effective dose refers to that amount of a therapeutic sufficient to result in a healthful benefit in the treated subject.

The precise dose of the therapeutic embodied by this invention, to be employed in the formulation, will depend on the route of administration, and the nature of the patient's disease, and should be decided according to the judgment of the practitioner and each patient's circumstances according to standard clinical techniques. The term "inhibit" or "inhibition" means to reduce by a measurable amount. The ability of a therapeutic composition or vaccine of the invention to produce this effect can be detected in vitro, e.g., using a transendothelial migration assay as previously described. Further experimental evidence of inhibition includes observing inhibition of inflammation in vivo in an animal model. Effective doses may thus be extrapolated from dose-response curves derived from animal model test systems.

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutics that exhibit large therapeutic indices are preferred. While therapeutics that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In Vitro Transmigration Assays

In a typical "transmigration assay" in tissue culture inserts, leukocytes are placed in suspension above an endothelial monolayer growing on a porous filter above a lower well of endogenous [made by the endothelium] or exogenous chemoattractant. The leukocytes that end up in the bottom chamber at the end of the assay are counted as transmigrated, and reagents that reduce their number are said to block transmigration. However, in order to get there, the leukocyte must bind to the endothelium, crawl to the nearby junction, diapedese across the endothelium, migrate through the subendothelial basal lamina, crawl through the filter support [usually many times thicker than the endothelium itself], and detach from the underside of the filter. Any reagent that blocks any step in this process would be considered to block transmigration.

For in vitro assays of transendothelial migration, endothelial cells (E.C.) are cultured on hydrated Type I collagen gels overlaid with fibronectin. Components of the culture medium penetrate into the porous gel. E.C. grown on the upper surface of a porous filter are suspended in a larger culture vessel. Culture medium is placed in the inner and outer chambers to reach the apical and basal surfaces of the monolayer, respectively. In the preferred collagen gel method, adherent leukocytes remaining on the apical surface can be distinguished visually from those that have transmigrated. Procedures have also been devised to strip off any leukocytes remaining bound to the apical surface of the monolayer. In the filter chamber method the percentage of the leukocytes added to the upper chamber that appear in the lower chamber is calculated by direct counting. However, in order to be counted as "transmigrated", a leukocyte must 1] attach to the apical surface of the endothelium, 2] migrate to the intercellular junction, 3] diapedese between the endothelial cells, 4] detach from the endothelial cells and penetrate their basal lamina, 5] crawl through the filter itself, and 6] detach from the filter and fall into the chamber below. Reagents that block any of these steps will therefore block the readout of transmigration in this system.

The preferred transmigration assay for use in accordance with this invention (i.e., the upper one) specifically distinguishes apical adhesion from transmigration (1, 5), and can even detect a block of transmigrated cells at the level of the subendothelial basal lamina (4).

Transendothelial Migration Assays

All HUVEC, PMN, Mo, and NK cells express PECAM in a unimodal distribution (5, 6, 11, 45). We have been unable to distinguish by surface markers or morphology any difference between those leukocytes that are blocked by anti-PECAM reagents and those that are not. Therefore, functional assays are used to uncover a role for alternative molecules in vivo HUVEC are cultured on hydrated collagen gels in Medium 199+20% normal human serum, as described (48) and the transendothelial migration assay is preferably run as previously published (1, 45). Migration of monocytes can be run in the presence or absence of cytokine stimulation of the endothelium. For experiments to study TEM of neutrophils, the HUVEC monolayer is activated by adding 3 I.U./ml of IL-1β to the culture medium for four hours prior to the assay.

Briefly, monocytes or neutrophils, freshly isolated from venous blood of healthy donors on Ficoll/Hypaque gradients, are allowed to settle on confluent HUVEC monolayers at 37° C. in the presence or absence of test reagents. Preferably the assays are run in Medium 199+0.1% human serum albumin, but there is no difference when run in complete medium (45). After sufficient time for TEM of the control group [generally 1 hour], the monolayers are washed vigorously with 1 mM EGTA to remove any leukocytes still adherent by divalent cation-dependent interactions [selectins or integrins] then rinsed in phosphate buffered saline with divalent cations and fixed in 2.5% glutaraldehyde overnight. This strengthens the collagen gel so that it is easier to manipulate when removed from the 96-well tray. These monolayers are stained with Wright-Giemsa and mounted on slides for direct observation under Nomarski optics.

Tight adhesion to the apical surface of the endothelial monolayer is the rate-limiting step in leukocyte emigration (45), and upon tight adhesion the emigration process becomes independent of shear stress (56). The absence of fluid shear stress in the culture system is therefore of little physiologic relevance, and predictions made based on this in vitro model have held up in several in vivo models (2, 6, 8, 9, 12). The key to this assay is to observe the leukocytes iii situ in relation to the confluent endothelial cell monolayer. Using Nomarski optics, one can distinguish by the plane of focus, leukocytes that are attached to the apical surface of the monolayer from those that have transmigrated. One can then quantitate the total number of leukocytes associated with the monolayer visually or by quantitation of fluorescently-labeled leukocytes (1, 45) to assess the effect of a reagent on adhesion to the endothelium. Transmigration is quantitated as the percentage of those leukocytes remaining associated with the monolayer that have migrated beneath the monolayer. Therefore, a measurement of TEM is independent of the degree of adhesion to the monolayer and the effects of antibodies or other reagents on adhesion and TEM can be assessed independently.

Obviously, if a leukocyte does not adhere to the endothelial surface, it cannot transmigrate. One could argue, for example, that the population of leukocytes that transmigrates normally in the presence of anti-CD18 might be a separate subpopulation or might be using a different pathway than the "CD18-dependent" leukocytes [that did not bind in the presence of mAb] would have used had they been able to adhere. To address this issue, one may repeat these experiments modifying the procedure as follows: Optimize cytokine activation conditions such that there are multiple adhesion receptors expressed on the endothelial surface [E- and P-selectin, ICAM-1, VCAM-1] such that blocking any particular one does not noticeably affect apical adhesion of the leukocyte population due to the redundancy of adhesion molecules. The TEM assay would be run under these conditions. If adhesion is minimally affected by the presence of the test mAb but TEM is reduced, one could conclude that the molecule in question played a role in TEM that was independent of its role in apical adhesion. Other modifications of the standard TEM assay will be discussed below in reference to particular situations.

The Role of CD99L2 in Transendothelial Migration

Purified Fab and F[ab']2 fragments of CD99L2 selectively prebound to leukocytes or endothelial cells can be used to determine on which cell the antigen is critical. This avoids potential problems with intact Fc-bearing antibody binding to leukocytes via their high affinity Fc receptors, or of turning endothelial cell monolayers into immune complexes and stimulating the adhesion of leukocytes via low affinity Fc receptors to mAb bound to endothelium. Dose-response experiments will determine the optimal blocking concentrations. These experiments are repeated on PMN.

To show that the leukocyte CD99L2 is critical for TEM, monocytes or PMN are incubated in suspension for 30 min at 4° C. with saturating concentrations of Fab fragments of CD99L2 [as determined by flow cytometry], then flashed free of unbound mAb. The leukocytes are added to untreated HUVEC monolayers and the TEM assay run as usual. As a positive control, one could run the TEM assay in the continued presence of optimal concentrations of CD99L2, conditions Clown to block TEM. If Fab fragments of CD99L2 bound to leukocytes alone block TEM as efficiently as Fab added to both cell types simultaneously, we would interpret this to mean that CD99L2 on the leukocyte was critical. This does not rule out a role for endothelial CD99L2, however. If CD99L2 added only to leukocytes blocked TEM very poorly, this would be consistent with the endothelial cell carrying the crucial CD99L2, possibly binding to a different molecule on the leukocyte. If CD99L2 added to the leukocytes blocked partially, this would suggest that CD99L2 on both leukocytes and endothelial cells was critical, but they bound to different molecules on the apposing cells.

To show that the endothelial CD99L2 is critical for TEM, confluent HUVEC monolayers are incubated with CD99L2 Fab or F[ab']2 fragments under conditions determined by immunofluorescence and flow cytometry to produce maximal and saturated staining of CD99L2 at the junctions. [For mAb against PECAM and VE-cadherin 1 hour at 4° C. is sufficient, but this can be determined empirically.] Unbound mAb are washed away, untreated Mo or PMN are added, and the co-culture warmed to 37° C. for the TEM assay. Again, positive controls are preferably run in the continued presence of optimal concentrations of CD99L2. If the block in TEM produced when CD99L2 is added only to endothelial cells is as great as the positive control where both cell types are exposed to the mAb, this indicates that CD99L2 on the endothelial cells is critical. A poor block under these conditions would suggest that CD99L2 on the endothelium is not important under these conditions. Again, an intermediate level of block would suggest that both leukocyte and endothelial CD99L2 are involved, perhaps binding to different molecules on each other.

The presence of CD99L2 on both leukocytes and endothelial cells suggests that CD99L2 on the leukocyte may interact in a homophilic way with CD99L2 on the endothelium. If optimal blockade of TEM can be achieved by binding the mAb to either leukocyte or endothelial cells, and there is no additive block when mAb is added to both, this would suggest that CD99L2 on leukocytes interacts directly with CD99L2 on endothelial cells, in a homophilic manner similar to PECAM-1. This can be tested directly with the cloned protein.

There are alternative explanations for an incomplete block in TEM in these experiments. The most common one is endocytosis or destruction of cell-bound mAb during the assay such that it falls to insufficient levels to block TEM. If there is incomplete block when mAb is prebound to cells in the above assays, this possibility can be tested by altering the TEM assay as follows: after prebinding CD99L2 to the desired cell type, unbound mAb is washed away and the cells are maintained at 4° C. Leukocytes are added to the HUVEC monolayers on ice and allowed to settle in the cold. Under these conditions, antibody is not metabolized as the leukocytes settle on the monolayer surface. In the cold they do not adhere firmly. When the majority of the cells have settled, the culture vessel is warmed rapidly to 37° C. in the incubator and the leukocytes adhere firmly and transmigrate within 5-10 minutes. Immunofluorescence microscopy demonstrates that the vast majority of mAb is still present on the cells at the end of this time. This adaptation of the method allows study of the effects of the added mAb before it is metabolized.

Another explanation for the inability of CD99L2 to block TEM when added only to one cell type is that the epitope of CD99L2 recognized by mAb CD99L2 is not the one used by that cell type. For example, if the amino terminus of endothelial CD99L2 interacts with an epitope of leukocyte CD99L2 that is close to the membrane, and the CD99L2 epitope is on the amino terminus of CD99L2, then one would expect that adding CD99L2 to HUVEC would block TEM, but adding CD99L2 only to leukocytes would not.

The position of CD99L2 in the order of adhesion events relative to PECAM can also be evaluated. When PECAM function is blocked, leukocytes remain tightly adherent to the endothelium at the cell borders even in the presence of EDTA. This suggests that they are binding by molecules other than the divalent cation-dependent integrin/ICAM interactions. If the leukocytes were bound via CD99L2, they would be released when the blocking mAb is added. This fits with the data in which CD99L2 partially blocked adhesion of Mo and PMN. If CD99L2 functioned at a step distal to PECAM, there would be no effect of adding mAb at this stage.

To show this, several series of experiments in which leukocytes are first arrested in TEM by anti-PECAM mAb are conducted. In the first series, CD99L2 or isotope control mAb are subsequently added in the continued presence of anti-PECAM. If bound leukocytes are released, CD99L2 is likely the molecule that binds leukocytes in the face of PECAM block. Failure to release leukocytes could be due to a variety of factors. Therefore, a second set of experiments are performed in which, following arrest of TEM by anti-PECAM mAb, the anti-PECAM reagents are washed out and CD99L2 or control mAb is added. Following washout of anti-PECAM mAb, TEM resumes normally and is complete within 30-90 min (1) in the absence of additional inhibitors. If CD99L2 functioned at a step proximal to PECAM, we do not expect to see any blockade, and TEM would be completed normally. However, if CD99L2 were involved in a step distal to PECAM, we expect the arrest of TEM to continue.

A third series of experiments can be conducted analogous to the second one in which the order of the application of the mAb would be reversed. TEM is first arrested by application of mAb CD99L2, then anti-PECAM mAb is added after CD99L2 is washed away. In these experiments anti-PECAM mAb should not prevent subsequent TEM when CD99L2 is washed away if it functions proximal to CD99L2, but should block if PECAM functioned distally. Since leukocytes blocked by anti-PECAM reagents remain tightly adherent to the endothelial cells, repeating the first series of experiments with the order of reagents reversed would not be instructive, but might be performed as an internal control.

Characterization of CD99L2

Clues to the complete function and importance of this molecule come from several straightforward assays (45, 48, 57-59). These biochemical and immunological studies complement the data derived from cloning and sequencing the molecule.

Rate of Biosynthesis and Turnover of this Protein

In pulse-chase experiments HUVEC monolayers pretreated for one hour in methionine- and cysteine-free medium are metabolically labeled with $^{35}$S-methionine and cysteine for one hour followed by a "chase" in nonradioactive medium. At various time points, cells are lysed and immunoprecipitation with CD99L2 and control mAbs to retrieve the CD99L2 and control antigens. These are analyzed by SDS-PAGE and subjected to autoradiography (48). The rate of synthesis and posttranslational modification is determined relative to other markers of the endothelial membrane such as PECAM-1, VE-cadherin [junctional molecules] and ICAM-1 or MHC Class I [diffusely expressed on the plasmalemma] by densitometry of the autoradiograms, or directly by excision of the radioactive bands from the gel (58, 59). The rate of turnover can be determined directly in separate experiments in which HUVEC are metabolically labeled to steady state, then radioactive medium is withdrawn. Immunoprecipitation from cell lysates is carried out at time points over two days and analyzed as above for the presence of radioactive CD99L2 and control cell markers.

Alternative Forms of CD99L2

Endothelial cells, monocytes, PMN, platelets, and lymphocytes are lysed and probed by Western blot with an anti-CD99L2 antibody. This approach has identified a 45 kD molecule by both Western blot and immunoprecipitation of HUVEC. However, HUVEC grown under different conditions [e.g. cytokine stimulation] may express alternatively spliced forms or CD99L2 that is glycosylated in a different manner than cells under resting conditions. This finding would suggest that CD99L2 had different [or enhanced] functions under these conditions which can be tested directly by running the TEM assay under those cytokine conditions. Leukocytes may express a structurally different molecule that bears the same CD99L2 epitope. If so, the molecule may have different interactions or signaling pathways on these cell types and more than one cDNA clone.

Association with Other Molecules

Under extraction conditions of 0.1% Nonidet P-40 in phosphate buffered saline, followed by washes of the immunoprecipitates in 0.5% NP-40+0.1% SDS, no other molecule copurified with CD99L2 from HUVEC lysates. Immune precipitation from leukocyte or EC lysates under different detergent conditions may reveal an association with other molecules that may transduce signals or link it to the cytoskeleton. These molecules are identified based on reactivity with commercially available antibodies to known signaling and structural molecules, and a first hypothesis about the signal transduction pathways or cytoskeletal elements that CD99L2 interacts with will be generated.

Changes in CD99L2 Expression in Response to Inflammatory Cytokines

CD99L2's involvement in inflammation suggests that CD99L2 may respond to inflammatory cytokines. ICAM-1 expression increases when HUVEC are stimulated by IL-1β, TNFα (45, 60). PECAM levels do not increase in the face of cytokine treatment, but IFNγ treatment causes redistribution of PECAM out of the junction toward the apical surface of the cell (61). In a specific assay, confluent HUVEC monolayers are treated with cytokines relevant to inflammation [e.g. IL-1β, 3-10 I.U./ml for 6 to 24 hours; IFNγ, 100 I.U./ml for 1 to 3 days] and immunofluorescence employed to evaluate for a change in expression or distribution. Known cytokine-responsive adhesion molecules [e.g. ICAM-1 and Class II MHC or PECAM, respectively] can be used as positive controls. Changes in expression level are quantifiable, e.g., by flow cytometry.

Identification of relevant changes in vitro provides evidence that they also occur in situ. Immunoperoxidase histochemistry can be used to determine cellular expression and distribution on vasculature in inflamed tissues from various organs of the human body and compare with its expression on vasculature from matched normal tissues. A wide variety of "waste tissues" are available for examination, e.g., from surgical pathology and autopsy specimens, or skill from patients with psoriasis. Lesional and nonlesional skin from the same person at the same time, and biopsies taken over the course of time, can be compared.

The Mechanism of Action of CD99L2

The predicted amino acid sequence of the molecule gives a clue to its potential functions, as seen for CD99 (FIG. 2). "Sequence gazing" provides a starting place for experimentation. The cloned molecule is expressed in a variety of mammalian cells to determine which function[s] expressing the molecule imparts to these cells, e.g., similar to experiments with the junctional adhesion molecules PECAM (7, 49, 53, 65) and VE-cadherin (29). Of particular importance are soluble forms of CD99L2, i.e., the extracellular domain or ligand binding portion thereof, which can be used as inhibitors of CD99L2 function. In a specific aspect, a CD99L2-Ig chimeras, analogous to the PECAM-Ig chimeric construct discussed infra, is prepared.

Expression of CD99L2 on both leukocytes and endothelium, suggests that it mediates homophilic interactions between these cells. This mediation is demonstrated in both short term [L cell aggregation assays] and long term [culture] assays as previously described (7, 29, 49, 53, 65).

L cells are a murine fibroblast cell line that show little tendency to spontaneously bind each other. Expression of exogenous adhesion molecules by transfection imparts on them the adhesive properties of those molecules. L cells transfected with CD99L2 cDNA are nonenzymatically resuspended by brief incubation in 10 mM EDTA, washed, and resuspended in buffer at 106 cells/ml. One ml of this suspension is placed in each well of a 24-well culture tray and placed on a gyrotory shaker at 90 rpm. At time zero and various time points up to an hour, aggregation is stopped by adding glutaraldehyde to a final concentration of 2%. If L cells expressing CD99L2 on their surfaces bind to each other, they will form aggregates that are quantitated in a hemacytometer. The temperature dependence and divalent cation dependency of the adhesion are easily tested in such an assay. Potential inhibitors of the adhesion are added at time zero and their effect on adhesion is quantitated. In particular, mAb CD99L2, which blocks transmigration of leukocytes, should block adhesion.

Since both EC and leukocytes have CD99L2, it is reasonable to hypothesize that CD99L2-mediated adhesion is homophilic. That is, a molecule of CD99L2 on one cell binds to a molecule of CD99L2 on the apposing cell. In order to test this hypothesis, two populations of L cells are mixed. CD99L2 transfectants are mixed in the aggregation assay with an equal number of fluorescently labeled parental cells. At the end of the assay aggregates are examined under the fluorescent microscope. If binding is homophilic, only CD99L2 transfectants should be in the aggregates, which would be nonfluorescent. If binding is heterophilic [CD99L2 binds to another molecule endogenously expressed on the L cell surface] then mixed aggregates of labeled and unlabeled cells will be seen (65). The assay is then repeated with the labeled populations switched.

These assays demonstrate that CD99L2-transfected L cells aggregate in a homophilic manner.

These assays can be repeated by mixing CD99L2 transfectants with leukocytes or endothelial cells, which putatively contain ligands for CD99L2. In this case CD99L2 transfectants bind to the leukocytes or endothelial cells in a manner that is blocked by adding CD99L2 to the transfectants, but not to the leukocytes or EC.

In long-term assays, transfected cells are mixed with non-transfected fibroblasts in culture, which again are distinguished by an exogenous label. The cells are co-cultured for a number of days then stained with CD99L2 to determine the distribution. If binding is homophilic at the junctions, then CD99L2 will be concentrated only at the borders that transfected cells make with each other and not at the borders made with nontransfected cells.

If interaction between the CD99L2 on endothelial cells and leukocytes is heterophilic, that raises the possibility that there are unique ligands on leukocytes for endothelial CD99L2 and on endothelial cells for leukocyte CD99L'. CD99L2 ligands on leukocytes and endothelial cells can be identified by mixing CD99L2 transfectants with large numbers of radiolabeled leukocytes and endothelial cells, respectively. The cells are lysed under mild detergent conditions and the lysates passed over a CD99L2-Sepharose column. This will bind CD99L2 and its attached ligand. The bound material is eluted and run on SDS-PAGE, Radioactive bands represent candidate CD99L2 ligands. These bands are cut from the gels and subjected to protein sequencing.

CD99L2 Function in TEM

CD99L2 has at least two functions relevant to inflammation. It is an adhesion molecule (FIG. 12) that could potentially bind leukocytes to endothelial cells. Antibodies generated against mouse CD99L2 block inflammation in vivo. Specifically, the migration of neutrophils and monocytes, the principle cellular mediators of acute and chronic inflammation, respectively, were prevented from entering the inflamed peritoneal cavity by prior injection of the anti-CD99L2 antibody (FIG. 7).

It is known that a rise in intracellular free calcium in endothelial cells is required for TEM (66). Blocking this rise will inhibit transmigration, but not adhesion of PMN to endothelial cells (66). Fluo3 [Molecular Probes, Eugene, Oreg.], or other $Ca^{++}$-sensitive reagents, can be used to determine whether an intracellular calcium flux takes place shortly after leukocyte/EC engagement. In a specific embodiment, confluent HUVEC monolayers are washed free of serum and incubated with Fluo3-AM [3.3 mM solubilized in Pluronic F-127 and DMSO] in heat-inactivated calf serum for 40 min. at room temperature. This diffuses into the cells where cytoplasmic esterases cleave the acetoxy methyl ester, rendering the dye membrane-impermeable. Sulfinpyrazone [0.25 mM] or probenecid [2.5 mM] is added to block organic anion transporters that pump the dye out of the cell and into endosomes (67). A rise in intracellular calcium produces a dramatic increase in fluorescence of Fluo3, which can be quantitated on our Cytofluor® instrument, visualized by fluorescence microscopy, or detected by flow cytometry on the FITC channel.

When leukocytes migrate across these Fluo3-loaded HUVEC monolayers, there is an increase in fluorescence due to an increase in cytosolic free calcium $\{[Ca^{++}]i\}$. This calcium flux may be blocked by CD99L2 mAb; if so, CD99L2 is responsible for generating this signal. CD99L2's direct involvement in calcium signaling can be tested by designing conditions in which CD99L2 transfectants reproduce the same phenomenon. If homophilic CD99L2 interactions between leukocyte and endothelium stimulate the rise in $[Ca^{++}]i$ then cross-linking CD99L2 on HUVEC by mAb could stimulate it as be.

Transmigration Assays in PECAM Defective Mice

We have recently produced transgenic mice that constitutively express soluble murine PECAM as a dimeric PECAM-IgG chimeric protein. Line $Tg8_{20}$ mice that have circulating concentrations of 20 µg/ml (which corresponds to the levels reached by doses of exogenously administered PECAM-IgG that block inflammation maximally) are healthy in the clean environment of the animal facility, but have a severely blunted acute inflammatory response. They only mobilize 10-20% of the PMN and monocytes that their wild-type littermates do. This suggests that a normal host does not become tolerized to therapeutic levels of this anti-PECAM reagent. These mice are valuable for studying the role of PECAM in chronic inflammation and the effect of chronic interference with PECAM function on the inflammatory response. These mice also demonstrate that expression of an inhibitor of inflammation (i.e., PECAM-IgG) at therapeutic levels does not inhibit basal inflammatory responses such as subclinical wound repair and does not render the mice immunodeficient. Thus, it is likely that therapeutic levels of anti-CD99L2 reagents could be administered chronically without untoward effects on cells involved in baseline immune function.

Various laboratories have established that PECAM plays a critical role in the TEM of neutrophils [PMN], monocytes [Mo], and natural killer [NK] cells. Inhibitors of PECAM function block the vast majority of TEM both in vitro (1, 4, 6, 7) and in vivo in several different models (2, 8-11). However, even under the most optimal conditions, we have never been able to block TEM more than 80-90% using monoclonal or polyclonal antibodies, soluble PECAM-IgG chimeras, or combinations thereof (4, 6). Even the $Tg8_{20}$ transgenic PECAM-IgG mice exposed constitutively to maximally therapeutic concentrations [20 mg/ml] still manage to mobilize 10-20% of their leukocytes in response to an acute inflammatory stimulus. These data suggest that PECAM-independent pathways normally exist and are responsible for this residual leukocyte emigration in the face of maximal PECAM blockade. In some inflammatory conditions, particularly chronic ones, this residual TEM may be enough to produce clinical symptoms in the face of maximally effective anti-PECAM therapy. Therefore, it is important to identify these alternative TEM pathways, determine how they function, and how to best inhibit them.

In a model of acute inflammation in which neutrophil emigration was stimulated by application of the chemotactic peptide formyl-methionyl-leucyl-phenylalanine [fMLP] directly on the mesentery of rats, anti-PECAM antibody did not block PMN extravasation, whereas the same antibody did block PMN extravasation when IL-1β was used to activate the endothelium of mesenteric venules (9). Thus, there is at least one stimulus that will elicit PECAM-independent leukocyte emigration in wild-type animals. Mice homozygous for a targeted deletion of PECAM-1 do not show any significant defects in a variety of acute inflammatory models when the deletion is made in the C57Bl/6 strain (26). These mice by definition use alternative mechanisms for TEM. However, when the same PECAM deletion is made in the FVB/n strain, the mice have a severe inability to respond to acute inflammatory stimuli, even though they are healthy at baseline (Schenkel et al., 2004, *J. Immunol.* 173:6403-6408).

Anti-PECAM therapy has been demonstrated to block TEM in the mesentery (2, 6, 8, 9) the lung (8), skin (8, 11), myocardium (10, 12), and probably the cornea (27). However, this leaves open the possibility that in other vascular beds the role of PECAM is less important. Most leukocyte emigration at sites of acute inflammation is across postcapillary venules. In the lung, however, emigration takes place across capillaries. In atherosclerosis and many forms of arteritis, leukocyte emigration takes place across arterial endothelium.

A formidable impediment to characterizing CD99L2 in vivo is that in wild-type mice anti-PECAM reagents block transmigration so well. Given the standard errors inherent in animal experiments, when anti-PECAM blocks 85±10% of leukocyte emigration, it may be very difficult to identify a block in the residual ~15%. Two different types of mice have accordingly been developed to study PECAM-independent pathway[s] of transmigration. In these mice all TEM takes place through PECAM-independent pathways. Mice of the C57Bl/6 strain with a targeted deletion of the PECAM-1 gene have normal leukocyte counts and only a very minor defect in their inflammatory response. These mice have developed in the absence of PECAM, so they must use alternative adhesion molecules for TEM. In addition, two independent lines of transgenic mice [$Tg5_{1000}$ and $Tg11_{1000}$] that constitutively express supratherapeutic levels of the soluble PECAM-IgG chimera have been developed, which circulates in their blood at 500 to 2,000 µg/ml. While the transgenic protein they express is perfectly active when transferred to wild-type mice, these mice are paradoxically resistant to its anti-inflammatory, effects. Since these mice have normal levels of endogenous PECAM on their leukocytes and endothelial cells, they must be using PECAM-independent pathways for TEM.

The normal inflammatory phenotype of the PECAM "knockouts" suggests that PECAM-independent pathways can be quantitatively expanded to support normal levels of TEM. The results with the $Tg5_{1000}$ and $Tg11_{1000}$ transgenic mice suggests that very high levels of circulating anti-PECAM reagents can desensitize the host over time to its anti-inflammatory effects. These transgenic mice are used to characterize more fully the CD99L2 pathways of TEM.

Screening and Chemistry

According to the present invention, nucleotide sequences derived from the gene encoding CD99L2, and peptide sequences derived from CD99L2, are useful targets to identify drugs that are effective in treating inflammatory conditions. Drug targets include without limitation (i) isolated nucleic acids derived from the gene encoding CD99L2; (ii) isolated peptides and polypeptides derived from CD99L2 polypeptides; isolated peptides and polypeptides derived from CDE99 binding partners; carbohydrate groups found on CD99L2; and small molecule mimetics or analogs thereof.

In particular, identification of CD99L2 as an important mediator of TEM provides for development of screening assays, particularly for high throughput screening of molecules that up- or down-regulate the activity of CD99L2. Accordingly, the present invention contemplates methods for identifying specific ligands of CD99L2 using various screening assays known in the art.

Any screening technique known in the art can be used to screen for CD99L2 agonists or antagonists. The present invention contemplates screens for small molecule ligands or ligand analogs and mimics, as well as screens for natural ligands that bind to and agonize or antagonize CD99L2 in vivo. Such agonists or antagonists may, for example, interfere in the adhesion properties or TEM properties of CD99L2, with resulting effects on CD99L2 function. For example, natural products libraries can be screened using assays of the invention for molecules that agonize or antagonize CD99L2 activity.

Knowledge of the primary sequence of CD99L2, and the similarity, of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, Science 1990, 249:386-390; Cwirla, et al., Proc. Natl. Acad. Sci. USA 1990, 87:6378-6382; Devlin et al., Science 1990, 49:404-406), very large libraries can be constructed ($10^6$-$10^8$ chemical entities). A second approach uses primarily chemical methods, of which the Geysen method (Geysen et al., Molecular Immunology 1986, 23:709-715; Geysen et al. J. Immunol. Meth. 1987, 102:259-274; and the method of Fodor et al. (Science 1991, 251:767-773) are examples. Furka et al. (14th International Congress of Biochemistry 1988, Vol. 5, Abstract FR:013; Furka, Int. J. Peptide Protein Res. 1991, 37:487-493), Houghton (U.S. Pat. No. 4,631,211) and Rutter et al. (U.S. Pat. No. 5,010,175) describe methods to produce a mixture of peptides that can be tested as agonists or antagonists.

In another aspect, synthetic libraries (Needels et al., Proc. Natl. Acad. Sci. USA 1993, 90:10700-4; Ohlmeyer et al., Proc. Natl. Acad. Sci. USA 1993, 90:10922-10926; PCT Publication Nos. WO 92/00252 and WO 9428028) and the like can be used to screen for CD99L2 ligands according to the present invention.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through conventional chemical, physical, and biochemical means (Blondelle et al., Tib Tech 1996, 14:60).

In Vitro Screening Methods

Candidate agents are added to in vitro cell cultures of endothelial cells, or to purified CD99L2 (preferably in a stable soluble form, e.g., expressed as a CD99L2/Ig chimeric construct), and their ability to bind to CD99L2 (particularly for a primary screen to identify candidate compounds), or more preferably their ability to inhibit binding of leukocytes to CD99L2, is evaluated. In endothelial cell culture systems, the ability to inhibit TEM can be evaluated.

A number of suitable in vitro systems are described above.

In Vivo Screening Methods

Intact cells or whole animals expressing a gene encoding CD99L2 can be used in screening methods to identify and further characterize candidate digs. Any of the animal models or transgenic animal models described above are suitable for screening of CD99L2 antagonists.

In one series of embodiments, a permanent cell line is established. Alternatively, cells (including Without limitation mammalian, insect, yeast, or bacterial cells) are transiently programmed to express an CD99L2 gene by introduction of appropriate DNA or mRNA, e.g., using the vector systems described above. Identification of candidate compounds can be achieved using any suitable assay, including without limitation (i) assays that measure selective binding of test compounds to CD99L2 (ii) assays that measure the ability of a test compound to modify (i.e., inhibit or enhance) a measurable activity or function of CD99L2 and (iii) assays that measure the ability of a compound to modify (i.e., inhibit or enhance) the transcriptional activity of sequences derived from the promoter (i.e., regulatory) regions the CD99L' gene.

In Vivo Testing Using Transgenic Animals

Transgenic mammals can be prepared for evaluating the molecular mechanisms of CD99L2. Preferably, for evaluating compounds for use in human therapy, the animals are "humanized" with respect to CD99L2. Such mammals provide excellent models for screening or testing drug candidates. The term "transgenic" usually refers to animal whose germ line and somatic cells contain the transgene of interest, i.e., CD99L2. However, transient transgenic animals can be created by the ex vivo or in vivo introduction of an expression vector of the invention. Both types of "transgenic" animals are contemplated for use in the present invention, e.g., to evaluate the effect of a test compound on CD99L2 activity.

Thus, "knock-in" mammals expressing human CD99, or human CD99L2, or both, can be prepared for evaluating the molecular biology of this system in greater detail than is possible with human subjects. It is also possible to evaluate compounds or diseases on human or murine CD99 "knockout" animals, e.g., to identify a compound that can compensate for a defect in human or murine CD99 activity. Both technologies permit manipulation of single units of genetic information in their natural position in a cell genome and to examine the results of that manipulation in the background of a terminally differentiated organism.

Although rats and mice, as well as rabbits, are most frequently employed as transgenic animals, particularly for laboratory studies of protein function and gene regulation in vivo, any animal can be employed in the practice of the invention.

A "knock-in" mammal is a mammal in which an endogenous gene is substituted with a heterologous gene (Roemer et al., New Biol. 1991, 3:331). Preferably, the heterologous gene is "knocked-in" to a locus of interest, either the subject of evaluation (in which case the gene may be a reporter gene; see Elefanty et al., Proc. Natl. Acad. Sci. USA 1998, 95:11897) of expression or function of a homologous gene, thereby linking the heterologous gene expression to transcription from the appropriate promoter. This can be achieved by homologous recombination, transposon (Westphal and Leder, Curr. Biol. 1997, 7:530, 1997), using mutant recombination sites (Araki et al., Nucleic Acids Res. 1997, 25:868) or PCR (Zhang and Henderson, Biotechniques 1998, 25:784). See also, Coffman, Semin. Nephrol. 1997, 17:404; Esther et al., Lab. Invest. 1996, 74:953; Murakami et al., Blood Press. Suppl. 1996, 2:36.

A "knockout mammal" is a mammal (e.g., mouse) that contains within its genome a specific gene that has been inactivated by the method of gene targeting (see, e.g., U.S. Pat. No. 5,777,195 and No. 5,616,491). A knockout mammal may be either a heterozygote knockout (i.e., one mutant allele and one wild-type allele) or a homozygous mutant (i.e., two mutant alleles). Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development 1995, 9:2623-34) describes PPCA knock-out mice.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo. However, the invention does not require any particular method for preparing a transgenic animal.

Generally, for homologous recombination, the DNA will be at least about 1 kilobase (kb) in length and preferably 3-4 kb in length, thereby providing sufficient complementary sequence for recombination when the construct is introduced. Transgenic constructs can be introduced into the genomic DNA of the ES cells, into the male pronucleus of a fertilized oocyte by microinjection, or by any methods known in the alt, e.g., as described in U.S. Pat. Nos. 4,736,866 and 4,870,009, and by Hogan et al., *Transgenic Animals A Laboratory Manual*, 1986, Cold Spring Harbor. A transgenic founder animal can be used to breed other transgenic animals; alternatively, a transgenic founder may be cloned to produce other transgenic animals.

Included within the scope of this invention is a mammal in which two or more genes have been knocked out or knocked in, or both. Such mammals can be generated by repeating the procedures set forth herein for generating each knockout construct, or by breeding to mammals, each with a single gene knocked out, to each other, and screening for those with the double knockout genotype.

Regulated knockout animals can be prepared using various systems, such as the tet-repressor system (see U.S. Pat. No. 5,654,168) or the Cre-Lox system (see U.S. Pat. No. 4,959,317 and No. 5,801,030).

High-Throughput Screen

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time. Such high-throughput screening methods are particularly preferred. The use of high-throughput screening assays to test for agents is greatly facilitated by the availability of large amounts of purified polypeptides, as provided by the invention.

EXAMPLES

The present invention will be better understood by reference to the following Examples, which are intended as illustrative of the invention and not limiting thereof.

Example 1

Murine CD99L2

Several murine cDNA libraries were probed with human CD99 cDNA clone to find mouse CD99.

A breakthrough came when the murine genome sequence began to accumulate in the public data base. From three ESTs and a genomic sequence cosmid (Genbank accession numbers AI466980, AW227546, AW320831, and AF125314, respectively) a putative open reading frame encoding a hypothetical protein designated XAP89 (X chromosome associated protein 89) was predicted that had several regions of high homology to human CD99 (Butcher, E. C. 1991 Cell 67:1033-1036). Its nucleotide sequence, however, was distinctly different from human CD99 due to alternative codon usage. This sequence was used to design primers to complete the sequence of the cDNA by 5'-RACE using a murine thymus cDNA library. One 843 bp cDNA clone (FIG. 1) encoded a 237 amino acid protein with significant homology to human CD99 along several highly conserved stretches of the protein, particularly in the transmembrane domain (FIG. 2). This protein is predicted to be a type I membrane protein, which, similar to human CD99 has several potential sites for O-glycosylation but none for N-linked glycosylation. The hydrophilicity plot of both molecules is similar. The size of the nonglycosylated protein is predicted to be 25.46 kD, which is somewhat larger than nonglycosylated human CD99 (18 kD). Comparison of this protein with those in the gene bank showed this molecule to be more homologous to human CD99L2 than human CD99. The closest match is a sequence subsequently filed as murine CD99L2 (GenBank accession no. AY078163). The murine form of this molecule is referred to in this application as murine CD99L2 or muCD99L2.

Transcripts for muCD99L2 were detected in bone marrow and thymus, as expected based on tissue expression of human CD99. COS cells transfected with a Flag-tagged version of our muCD99L2 clone expressed it on the cell surface concentrated at the cell borders, as expected based on the localization of human CD99 (2). Murine CD99L2 purified from transfected cells was used to inoculate rabbits to produce anti-muCD99L2 antibodies. Immunoglobulin from an immunized rabbit stained the same transfected COS cells in a junctional pattern demonstrating specific staining (FIG. 3). The same antiserum stained monocytes, lymphocytes, granulocytes, and erythrocytes from mouse peripheral blood—all cells known to bear CD99 in humans (not shown). Moreover, specific staining was seen on vascular endothelial cells, and weaker staining on vascular smooth muscle cells, similar to what has been found with human CD99 (FIG. 4).

Figure 6:
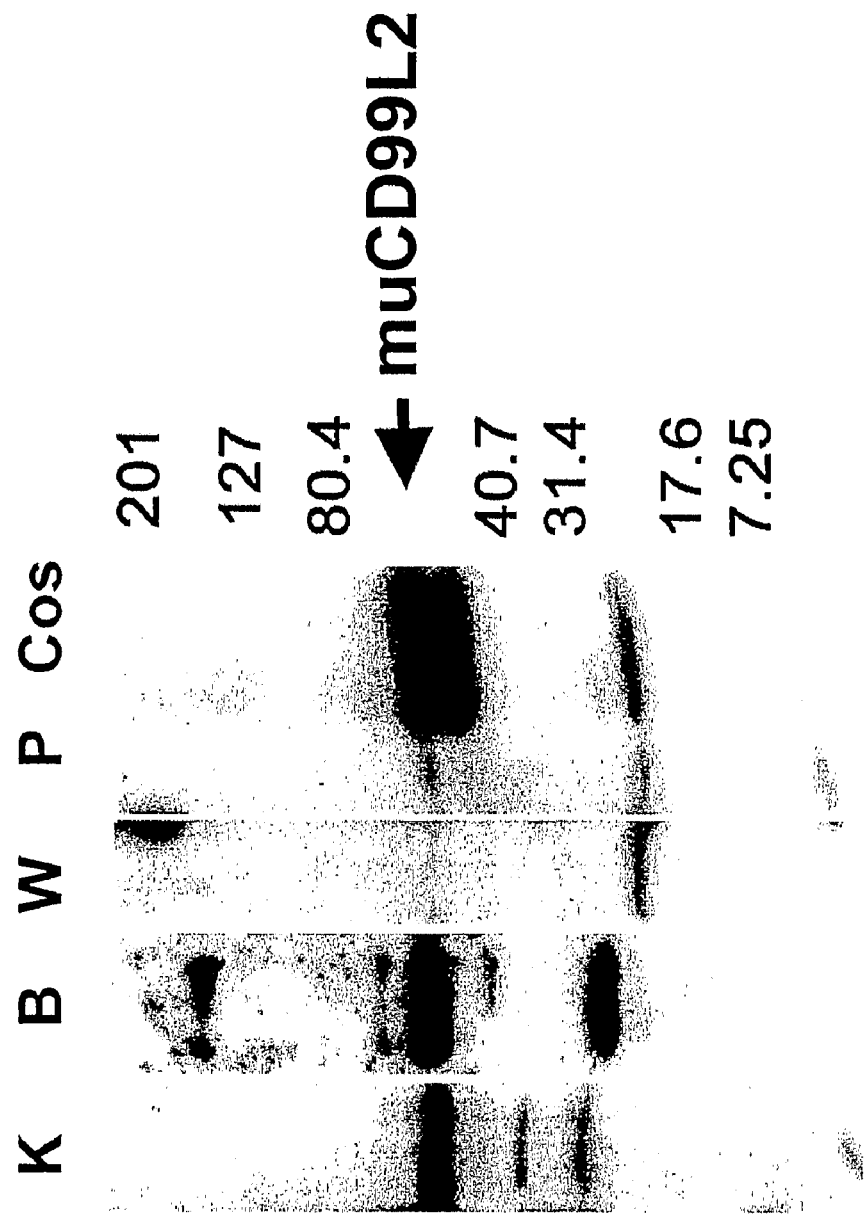
FIG. 6. Expression of murine CD99L2 in mouse tissues and cells. Western blot analysis using the rat anti-muCD99L2 antiserum detects a protein of approximately 45 kD in lysates of kidney (K), whole blood (B), purified leukocytes (W), and peritoneal lavage cells (P) that co-migrates with the protein expressed by COS cells transfected with the muCD99L2 cDNA. No such band was detectable in non-transfected COS (not shown). Note that the numbers of leukocytes in the purified leukocyte and peritoneal lavage samples was approximately 1/10 of that in the whole blood. The doublet in the COS cell lysate may represent alternatively differentially glycosylated forms. Bands from different blots are compared in this figure.

Immunized rats were used for producing monoclonal antibodies. Immunoglobulin from immunized rats stained leukocytes and red blood cells (FIG. 5). Fortunately for our in vivo studies, expression of muCD99L2 on RBCs is very low, allowing use of the rat antisera for preliminary studies. Immunoblotting from murine tissues revealed a single band with apparent molecular weight of approximately 45 kD, similar in size to the electrophoretic mobility of the cloned gene product in transfected COS cells (FIG. 6). Therefore, the inventors have identified, cloned, and developed reagents that identify muCD99L2.

Example 2

The Role of muCD99L2 in Transmigration In Vivo

Preliminary data showed that the rat anti-muCD99L2 sera could block inflammation in the thioglycollate peritonitis model. Anti-muCD99L2 serum, but not normal rat serum, blocked PMN accumulation by 60% and reduced monocyte influx to near background levels (FIG. 7) measured 18 hours after thioglycollate administration. Similar data were obtained with the polyclonal rabbit IgG.

Figure 8:
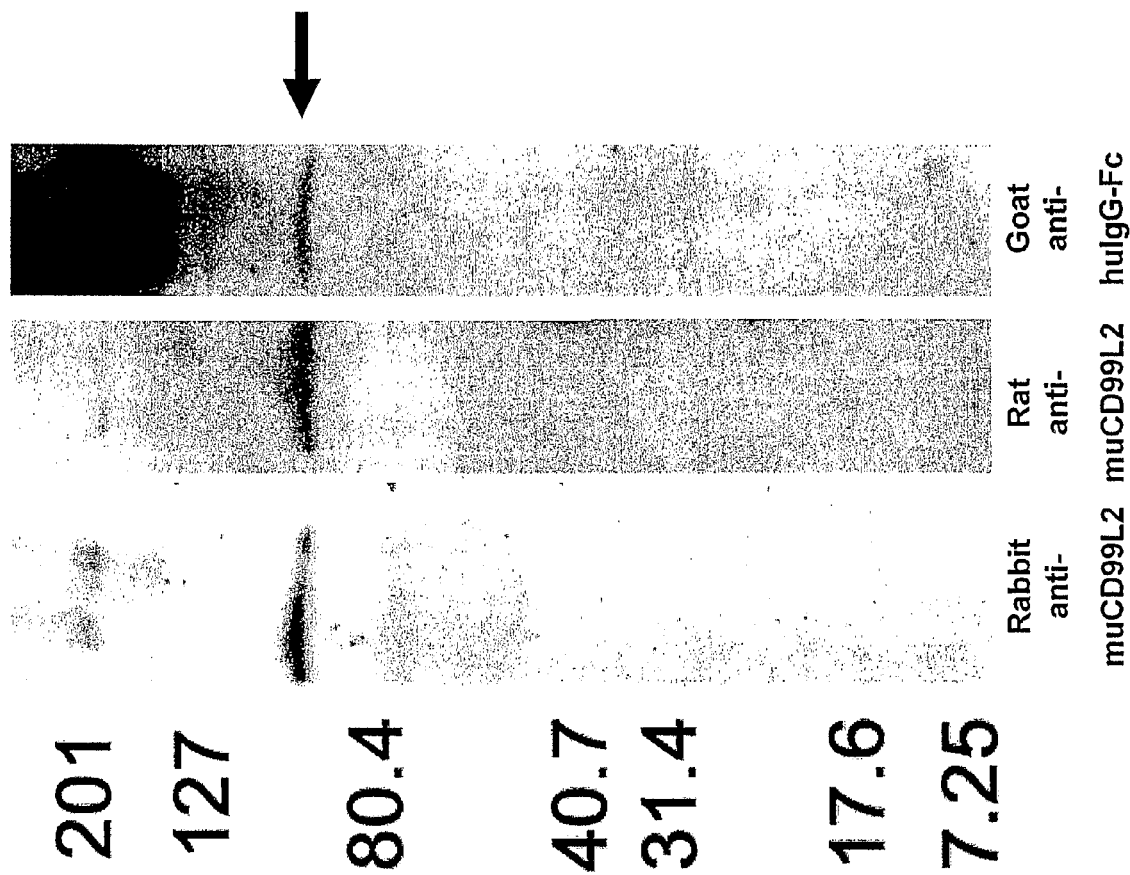
FIG. 8. Expression of muCD99L2-Fc. Culture supernate from COS cells stably transfected with a cDNA construct encoding a muCD99L2-Fc chimera was subjected to SDS-PAGE and Western blotting for expression of the molecule. A single band running at the expected Mr of 100 kD (for the dimerized form) was detectable by our rabbit and rat antisera against muCD99L2 as well as by a goat antibody specific for the Fc portion of human IgG. The band at 150 kD in the right lane represents cross-reactivity of the anti-human IgG with bovine IgG present in the culture medium.

We have also developed a muCD99L2-Fc chimera in which the extracellular domain of CD99 is fused to the Fc portion of human IgG1. We have successfully used a similar PECAM-Fc chimera to block transmigration at the PECAM-dependent step in vitro (34) and in vitro (35, 36). The muCD99L2-Fc chimera, purified from transfected cell supernate, runs at the expected Mr of 100 kD (for the dimer) on SDS-PAGE (FIG. 8). Due to the high level of expression of muCD99L2 on leukocytes and low level of expression of muCD99L2 on RBCs (See FIG. 5), this reagent has the desired properties of binding to leukocytes but not RBCs (not shown).

Example 3

Anti-muCD99L2 Monoclonal Antibody Production

Female Fisher rats were immunized intraperitoneally with 100 μg muCD99L2-Flag protein produced in COS cells and boosted with the same material twice. Four days after the final boost the spleen was harvested from individual rats and spleen cells aseptically fused with Y3 rat myeloma cells using polyethelene glycol. Viable hybrid cells were plated at a density of $1 \times 10^5$ cells per well in 11 Costar 96-well plates (using only the middle 60 wells per plate) in HAT medium.

Hybridoma supernates from wells in which there was abundant cell growth were screened by immunperoxidase cytochemistry as previously described (Muller et al., 1989, J. Exp. Med. 170, 399-414). Briefly, cultured monolayers of COS cells expressing muCD99L2 or parental cells are fixed in paraformaldehyde and air dried. Two μl droplets of hybridoma culture supernate were placed on top of the cells at positions identified by a grid drawn on the back of the culture dish. After 30 minutes of incubation at room temperature, the dishes were washed and incubated sequentially (for 30 min. each incubation with extensive washing in between antibodies) in rabbit anti-rat IgG, swine anti-rabbit IgG, and soluble complexes of rabbit anti-peroxidase with horseradish peroxidase (HRP). The reactivity of individual hybridoma supernates was detected by developing the HRP reaction with diaminobenzidine-$H_2O_2$.

Hybridomas producing supernates that stained muCD99L2-transfected COS, but not parental COS cells were considered positive. The assay was repeated and six hybridomas testing positive on both screens were expanded on thymocyte feeder layers for cloning. In the meantime, these expanded cultures were tested for reactivity against muCD99L2 by flow cytometry using live, non-permeabilized cells. Two of the six hybridomas consistently stained muCD99L2-transfected COS cells, muCD99L2-transfected L cells, and murine leukocytes.

Figure 11:
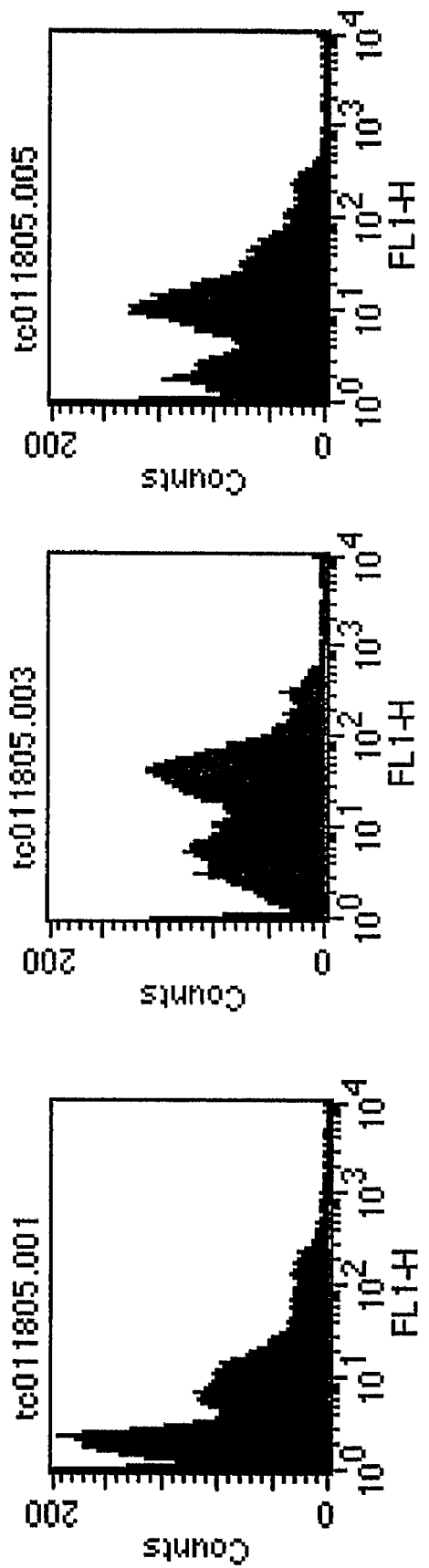
FIG. 11A-11C. in mAb 9G5 recognizes a major subpopulation of mouse leukocytes. Heparinized mouse blood was incubated with (A) normal rat serum, (B) MEC13.3 (monoclonal rat anti-mouse PECAM), or (C) 9G5 (monoclonal rat anti-mouse CD99L2) for 30 minutes, then RBC were lysed, cells were washed, and incubated with AlexaFluor 488-labeled goat anti-rat IgG for flow cytometric analysis.

Stable clones were produced from a hybridoma (9G5) that recognizes muCD99L2. This hybridoma produces anti-CD99L2 mAb (FIG. 9). 9G5 specifically stains muCD99L2-transfected cells, since it did not react with untransfected COS cells (not shown). mAb 9G5 also reacts selectively with muCD99L2-transfected L cells. Dilute culture supernates of mAb 9G5 (1:100 dilution) were reacted with control L cells (FIG. 10A) or muCD99L2-transfected L cells (FIG. 10B) detected with fluorescent secondary anti-rat IgG. More intense staining was seen with more concentrated supernate on the transfected cells, but not on the control cells. Heparinized mouse blood was incubated with normal rat serum (FIG. 11A), MEC13.3 (rat anti-mouse PECAM; FIG. 11B), or 9G5 (rat anti-mouse CD99L2; FIG. 11C) for 30 minutes, then RBC were lysed, cells were washed, and incubated with AlexaFluor 488-labeled goat anti-rat IgG for flow cytometric analysis. FIG. 11 reveals that mAb 9G5 recognizes a major subpopulation of mouse leukocytes.

Example 4

Expression of muCD99L2 Imparts Adhesive Capacity

Non-enzymatically resuspended L cell fibroblasts do not adhere to each other. When these same cells are transfected with PECAM (Muller et al., 1992, J. Exp. Med. 175:1401-1404) or human CD99 (Schenkel et al., 2002, Nature Immunol. 3:143-150), expression of these molecules imparts on them the ability to adhere to each other in a manner that depends on the function of that particular adhesion molecule.

Figure 12A:
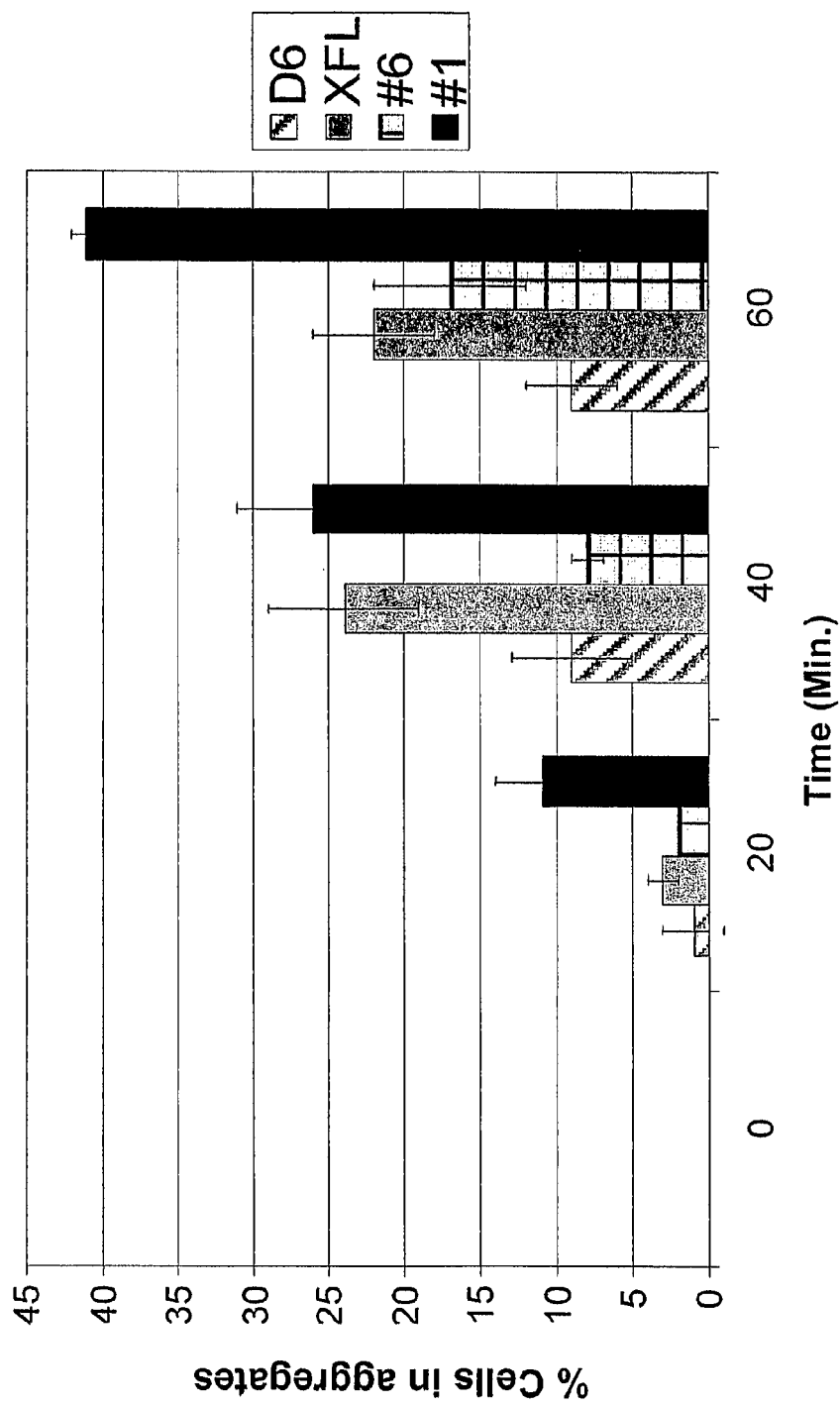

The ability of L cells transfected with muCD99L2 (XFL1 cells; FIG. 12A) to aggregate was tested. L cells transfected with human CD99 served as a positive control, and cells transfected with human PECAM in the antisense orientation served as a negative control.

The transfected L cells were washed in serum-free medium and resuspended by incubating in Hanks' Balanced Salt Solution (HBSS) containing 10 mM EDTA until they could be gently pipetted off the dish surface with minimal loss in cell viability. The resuspended cells were washed in cold HBSS, and resuspended to a concentration of $1 \times 10^6$/ml in warm HBSS containing divalent cations. One ml of cell suspension was transferred per well of a 24-well culture plate for each sample tested. The plate was incubated on a gyrotory shaker (90 rpm) at 37° for the times indicated. To stop the reaction, glutaraldehyde was added to the well to a final concentration of 2%. Then resuspended samples were examined in a hemacytometer chamber. The number of single cells and aggregates ($\geq$3 cells stuck together) was quantitated for all nine squares in the hemacytometer chamber for each sample (Muller et al., 1992, J. Exp. Med. 175:1401-1404).

In the presence of physiologic levels of $Ca^{+2}$ and $Mg^{+2}$ (1 mM and 0.5 mM, respectively), CD99L2-transfected L cells aggregated in a time-dependent manner to a similar extent as the positive control human CD99-transfected L cells (FIG. 12A). In contrast, the control L cells transfected with vector only did not aggregate appreciably. Additional experiments can be performed to determine whether the adhesive interactions of muCD99L2 are heterophilic or homophilic, whether adhesion requires divalent cations, and whether it can be blocked by purified anti-CD99L2 mAb, 9G5.

Example 5

Transgenic Mouse Studies of muCD99L2 in TEM

The role of muCD99L2 in TEM is tested in two separate models of acute inflammation in which a block in adhesion of leukocytes to endothelium can be distinguished from a block in TEM. The assays are the thioglycollate broth peritonitis assay and the croton oil ear swelling assay. In each assay, the effect of blocking the molecule is quantitatively assessed for a role selectively on diapedesis. The role of muCD99L2 in wild-type mice is examined to see what effect blocking it alone has on inflammation. The role of muCD99L2 in $Tg8_{20}$ mice, in which PECAM function is maximally blocked is evaluated to see whether they complement the PECAM block, or require PECAM blockade to function. The role of muCD99L2 in $Tg5_{1000}$ and $Tg11_{1000}$ mice is evaluated to see how they function under conditions where PECAM is not working, and in PECAM knockout mice to see how they function in the absence of PECAM. These latter two conditions may bring out roles for muCD99L2 that might not be obvious in wild-type mice where PECAM has a predominant role in TEM in these two animal models.

The Thioglycollate Broth-Induced Peritonitis Model

This model assesses the role of PECAM in TEM (2, 6) and other adhesion molecules (72-74) in acute inflammation. Reagents [blocking mAb or CAM-IgG chimeras] are injected systemically and tested for their ability to block entry of leukocytes into the peritoneal cavity. The mesentery is harvested and examined microscopically to determine whether the block was at the level of adhesion or TEM. In several previous studies, this has strikingly demonstrated an arrest of leukocytes on the endothelium of mesenteric venules when TEM was blocked by mAb against PECAM (2) or mPECAM-IgG (6), but not when adhesion was blocked by mAb against CD11b. Test mAb or isotype control IgG are injected intravenously by tail vein. One hour later 1 ml of 4% thioglycollate broth is injected i.p. via 26G ⅜" needle. The response to thioglycollate is tested at 18 hours in order to see the effect of the experimental perturbations on both PMN and monocytes. Time courses are adjusted to shorter times [4-12 hours] in order to make the effect on PMN more pronounced and later times [up to 4 days] when the effect on Mo is more pronounced. At the time of assay, the mice are sacrificed. Peritoneal cells are isolated by lavage in Hanks' Balanced Salt Solution. Total peritoneal cell numbers are quantitated and differential counts are performed on Wright-Giemsa-stained cytospins. Peripheral blood is collected for total WBC count and differential smear. It is important to be certain that a decrease in leukocytes entering the peritoneal cavity is not due to reduced numbers in the circulation. Selected organs are also harvested at this time, including the mesentery, which is fixed in formalin for histologic examination.

The Croton Oil Dermatitis Assay

This is an assay of nonspecific inflammation in which 10 ml of croton oil [2% in a 4:1 mixture of acetone:olive oil] is applied to one ear of a mouse (72). The contralateral ear receives 10 ml of carrier and serves as an internal control for background inflammation. Croton oil produces an acute inflammatory response in which the affected ear becomes red and swollen. Histologically, there is mast cell degranulation and recruitment of leukocytes out of the local venules into the soft tissues in the dermis of the ear. In our hands maximum leukocyte emigration [predominantly PMN] occurs 8 hours after application of the irritant. Reagents to be tested for their ability to block TEM are injected intraperitoneally one hour before application of croton oil.

Mice are sacrificed, both ears removed, and several cross-sections are examined to quantitate leukocyte efflux. This can be done manually or using image analysis software to quantitate $PMN/mm^2$. Alternatively, anti-PMN mAb with a fluorescent tag can be applied, and total fluorescence quantitated using a phosphorimager. Careful histologic examination of the ears will also tell us whether the block is at the level of TEM or adhesion. Blocking TEM results in accumulation of PAIN on the venular walls. This is also a good system in which to test the possibility that PECAM lockout or PECAM resistant mice [high dose transgenics] emigrate via a different vascular route [e.g. capillaries rather than venules], since the leukocytes tend to stay relatively close to the vessels they emigrated from in this model.

The Role of CD99L2 in TEM

Monoclonal antibodies (mAbs) against the murine form of CD99L2 are tested for their ability to block in these models. mAbs against muCD99L2 are expected to inhibit TEM in vivo the way human CD99 inhibits TEM of human cells in vitro. Purified, sterile, endotoxin-free Fab and F[ab']2 fragments of mAb against murine CD99L2 are tested.

Wild-type mice. Since human CD99 blocks TEM in the absence of PECAM blockade, the murine form is expected to would work similarly in vivo. Leukocyte emigration is markedly inhibited by optimal concentrations of mAb against murine CD99L2. The ears and mesenteric venules of mice are examined. A selective block in TEM should result in an increase in leukocytes on the vessel wall that reflects the decreased emigration of these cells. However, if CD99L2 is involved in an earlier stage of TEM than PECAM, it is possible that blocking CD99L2 in vivo will not produce the phenotype of leukocytes arrested on the vessel wall. If interruption of interaction with CD99L2 does not leave them firmly adherent to the endothelium by some other mechanism, they may be carried off in the flow of the bloodstream, and the phenotype produced in vitro under static conditions would not be seen, despite a dramatic reduction in leukocytes that emigrate.

$Tg8_{20}$ mice. The combined action of CD99L2 and anti-PECAM antibody bears testing in vivo. It is clinically important to know whether blocking any two molecules on leukocytes or endothelium could produce such a complete block in vivo. Blocking murine CD99L2 and murine PECAM is expected to produce a near-total block in leukocyte emigration. This is tested by injecting mAb against murine CD99L2 into the $Tg8_{20}$ and PECAM-deficient mice in the FVB/n background mice, in whom PECAM is maximally blocked. It may be difficult, if not impossible, to discern the site of the blockade in vivo, since the $Tg8_{20}$ and PECAM-deficient mice in the FVB/n background mice already show so many of their leukocytes arrested on the vessel wall. However, the quantitative decrease in leukocytes in the peritoneal cavity or the dermis of the ear should be noticeable.

$Tg5_{1000}$ and $Tg11_{1000}$ mice. In these mice PECAM-independent pathways of TEM predominate, since these mice do not seem to use their own PECAM. Monoclonal Ab against murine CD99L2 may have an even larger effect than in the wild-type mice. The same caveat about potentially blocking adhesion more than transmigration under flow conditions holds here as it did for wild-type mice.

PECAM-deficient [knockout] mice in the C57Bl/6 background. PECAM knockout mice must use PECAM-independent pathways for TEM. They mobilize the same numbers and types of leukocytes to sites of inflammation as wild-type mice, so they have expanded their use of these pathways to support normal levels of TEM. Under these conditions, it is simple to see an effect of blocking an alternate adhesion molecule. It is be instructive to determine whether the molecules knockout mice use for TEM are the same as those used by mice that have PECAM, but cannot use it [e.g., $Tg5_{1000}$ and $Tg11_{1000}$].

Example 6

Production of a muCD99L2 "Knockout" Mouse

Construction of the targeting vector to produce the muCD99L2 knockout mice in the C57Bl/6 background was complicated, requiring the litigation of large stretches of murine genomic DNA interspersed with LoxP sites. The strategy was to make a targeting vector that could be used to make a traditional "knockout" mouse (replacing muCD99L2 by homologous recombination) as well as an inducible transgenic mouse, in case the genome-wide excision of muCD99L2 results in embryonic lethality.

Figure 13:
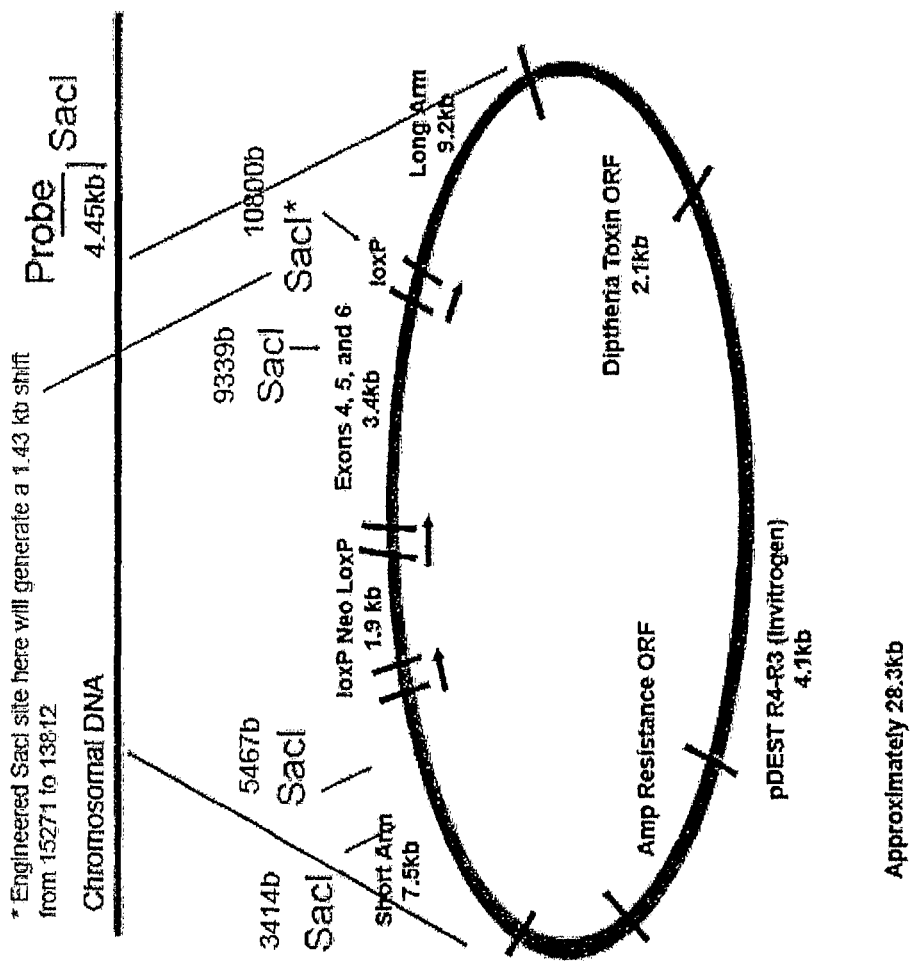
FIG. 13. Schematic representation of targeting vector to integrate a defective copy of muCD99L2 into mouse ES cells. This vector can be used to make a traditional "knockout" mouse (replacing muCD99L2 by homologous recombination) as well as an inducible transgenic mouse. The vector is designed to integrate around exons 4-6. In the native state the Neo cassette destroys the reading frame and ablates the gene. With the Neo cassette removed at the ES cell stage by exposure to Cre recombinase, the targeting vector recombines into mouse genomic DNA, reconstituting a functional gene. Upon subsequent exposure to Cre recombinase in the adult mouse, exons 4-6 and the intervening introns are deleted, creating a conditional "knockout." A SacI site has been engineered into the 3' loxP site so that insertion of the vector into genomic DNA can be detected by a probe designed to hybridize to the genome immediately 3' of the insertion. Digestion of genomic DNA with SacI produces a 15.2 kb band from this region. Upon plasmid integration, this restriction fragment length becomes 13.8 kb.

The targeting vector places exons 4-6 of muCD99L2 between long and short arms of intronic DNA from the muCD99L2 gene (FIG. 13). A neomycin resistance cassette is present to positively select for embryonic stem cells into which the targeting vector has been properly inserted, while the downstream cassette encoding diphtheria toxin A fragment will be brought along with integration events that are not homologous recombinations. ES cells harboring these unwanted events will therefore not grow in culture.

If attempts to delete muCD99L2 by homologous recombination result in embryonic lethality, the "Cre-Lox" method can be used with the same construct to make an inducible knockout. In this case, the Neomycin resistance gene is deleted from the LoxP sites by transiently transfecting Cre recombinase into the ES cells and selecting for clones that have selectively eliminated the Neo resistance cassette. The resulting ES cells will be injected into blastocysts of transgenic mice expressing Cre recombinase. This recombinase will specifically cut LoxP sites in the DNA resulting in deletion of the part of the genome between them—in this case exons 4-6 of murine CD99L2. Transgenic mice exist that express the Cre recombinase in an inducible form in a tissue- (and even cell-) restricted manner. Thus, the knockout can be targeted to endothelial cells only or leukocytes only.

Due to the large size of the targeting construct, restriction enzymes that would allow this vector to be built up piece-wise from smaller fragments are not available. The MultiSite Gateway Cloning system (Invitrogen) takes advantage of bacteriophage integration sites to allow the simultaneous ligation of multiple DNA fragments.

The vector is tested to ensure that the probe will detect it when it has incorporated into genomic DNA, and that the sequence of muCD99L2 in the ES cells contains no polymorphisms that would alter restriction enzyme sites critical for the detection of integration.

REFERENCES

1. Muller, W. A., S. A. Weigl, X. Deng, and D. M. Phillips. 1993. PECAM-1 is required for transendothelial migration of leukocytes. J. Exp. Med. 178:449-460.
2. Bogen, S., J. Pak, M. Garifallou, X. Deng, and W. A. Muller. 1994. Monoclonal antibody to murine PECAM-1 [CD31] blocks acute inflammation in vivo, J. Exp. Med. 179:1059-1064.
3. Berman, M. E. and W. A. Muller, 1995. Ligation of platelet/endothelial cell adhesion molecule 1 (PECAM-1/CD31) on monocytes and neutrophils increases binding capacity of leukocyte CR3 (CD11b/CD18). J. Immunol. 154:299-307.
4. Liao, F., H. K. Huynlh, A. Eiroa, T. Greene, E. Polizzi, and W. A. Muller. 1995. Migration of monocytes across endothelium and passage through extracellular matrix involve separate molecular domains of PECAM-1. J. Exp. Med. 182:1337-1343.
5. Berman, M. E., Y. Xie, and W. A. Muller. 1996. Roles of platelet/endothelial cell adhesion molecule-1 (PECAM-1, CD31) in natural killer cell transendothelial migration and beta 2 integrin activation. J. Immunol. 156:1515-1524.
6. Liao, F., J. Ali, T. Greene, and W. A. Muller. 1997. Soluble domain 1 of platelet-endothelial cell adhesion molecule (PECAM) is sufficient to block transendothelial migration in vitro and in vivo. J. Exp. Med. 185:1349-1357.
7. Muller, W. A., T. Greene, and F. Liao. 1997. Transendothelial migration and interstitial migration of monocytes are mediated by separate domains of monocyte CD31. In Leukocyte Typing VI. Proceedings of the VIth International Leukocyte Differentiation Antigen Workshop, Kobe, Japan, 1996. T. Kishimoto, editor. Garland Publishers, London. 370-372.
8. Vaporciyan, A. A., H. M. Delisser, H.-C. Yan, I. I. Mendiguren, S. R. Thom, M. L. Jones, P. A. Ward, and S. M. Albelda. 1993. Involvement of platelet-endothelial cell adhesion molecule-1 in neutrophil recruitment in vivo. Science 262:1580-1582.

9. Wakelin, M. W., M.-J. Sanz, A. Dewar, S. M. Albelda, S. W. Larkin, N. Boughton-Smith, T. J. Williams, and S. Nourshargh. 1996. An anti-platelet/endothelial cell adhesion molecule-1 antibody inhibits leukocyte extravasation from mesenteric microvessels in vivo by blocking the passage through basement membrane. J. Exp. Med. 184:229-239.
10. Murohara, T., J. A. Delyani, S. M. Albelda, and A. M. Lefer. 1996. Blockade of platelet endothelial cell adhesion molecule-1 protects against myocardial ischemia and reperfusion injury in cats. J. Immunol. 156:3550-3557.
11. Christofidou-Solomidou, M., M. T. Nakada, J. Williams, W. A. Muller, and H. M. Delisser. 1997. Neutrophil platelet endothelial cell adhesion molecule-1 participates in neutrophil recruitment at inflammatory sites and is down-regulated after leukocyte extravasation. J. Immunol. 158:4872-4878.
12. Gumina, R. J., J. E. Schultz, Z. Yao, D. Kenny, D. C. Warltier, P. J. Newman, and G. J. Gross. 1996. Antibody to platelet/endothelial cell adhesion molecule-1 reduces myocardial infarct size in a rat model of ischemia-reperfusion injury. Circulation 94:3327-3333.
13. Ross, R. 1993. The pathogenesis of atherosclerosis: a perspective for the 1990s. Nature 362:801-809.
14. Lasky, L. A. 1992. Selectins: Interpreters of cell-specific carbohydrate information during inflammation. Science 258:964-969.
15. Springer, T. A. 1994. Traffic signals for lymphocyte recirculation and leukocyte emigration: The multistep paradigm. Cell 76:301-314.
16. Lo, S. K., S. Lee, R. A. Ramos, R. Lobb, M. Rosa, G. Chi-Rosso, and S. D. Wright. 1991. Endothelial-leukocyte adhesion molecule 1 stimulates the adhesive activity of leukocyte integrin CD3 [CD11B/CD18, Mac-1, alpha m beta 2] on human neutrophils. J. Exp. Med. 173:1493-1500.
17. Lorant, D. E., K. D. Patel, T. M. McIntyre, R. P. McEver, S. M. Prescott, and G. A. Zimmerman. 1991. Coexpression of GMP-140 and PAF by endothelium stimulated by histamine or thrombin: A juxtacrine system for adhesion and activation of neutrophils. J. Cell Biol. 115:223-234,
18. Hermanowski-Vosatka, A., J. A. G. Van Strijp, W. J. Swiggard, and S. D. Wright. 1992. Integrin modulating factor-1: A lipid that alters the function of leukocyte integrins. Cell 68:341-352.
19. Tanaka Y., D. H. Adams, S. Hubscher, H. Hirano, U. Siebenlist, and S. Shaw. 1993. T-cell adhesion induced by proteoglycan-immobilized cytokine MIP-1 beta. Nature 361:79-82.
20. Huber, A. R., S. L. Kunkel, R. F. Todd, III, and S. J. Weiss. 1991. Regulation of transendothelial neurophil migration by endogenous interleukin-8. Science 254:99-102.
21. Tanaka, Y., S. M. Albelda, K. J. Horgan, G. A. Van Seventer, Y. Shimizu, W. Newman, J. Hallam, P. J. Newman, C. A. Buck, and S. Shaw. 1992. CD31 expressed on distinctive T cell subsets is a preferential amplifier of beta1 integrin-mediated adhesion. J. Exp. Med. 176:245-253.
22. Piali, L., S. M. Albelda, H. S. Baldwin, P. Hammel, R. H. Gisler, and B. A. Imhof. 1993. Murine platelet endothelial cell adhesion molecule (PECAM-1/CD31) modulates beta2 integrins on lymphokine-activated killer cells. Eur. J. Immunol. 23:2464-2471.
23. Meerschaert, J. and M. B. Furie. 1994. Monocytes use either CD11/CD18 or VLA-4 to migrate across human endothelium in vitro. J. Immunol. 152:1915-1926.
24. Newman, P. J., M. C. Berndt, J. Gorski, G. C. White II, S. Lyman, C. Paddock, and W. A. Muller. 1990. PECAM-1 [CD31] cloning and relation to adhesion molecules of the immunoglobulin gene superfamily. Science 247:1219-1222.
25. Sun, Q.-H., H. M. Delisser, M. M. Zukowski, C. Paddock, S. M. Albelda, and P. J. Newman. 1996. Individually distinct Ig homology domains in PECAM-1 regulate homophilic binding and modulate receptor affinity. J. Biol. Chem. 271:11090-11098.
26. Duncan, G. S., D. P. Andrew, H. Takimoto, S. A. Kaufman, H. Yoshida, J. Spellberg, J. L. de la Pompa, A. Elia, A. Wakeham, B. Karan-Tamir, W. A. Muller, G. Sendali, M. M. Zukowski, and T. W. Mak. 1999. Genetic evidence for functional redundancy of platelet/endothelial cell adhesion molecule-1 (PECAM-1): CD31-deficient mice reveal PECAM-1-dependent and PECAM-1-independent functions. J. Immunol. 162:3022-3030.
27. Tang, Q. and R. L. Hendricks. 1996. Interferon gamma regulates platelet endothelial cell adhesion molecule-1 expression and neutrophil infiltration into herpes simplex virus-infected mouse corneas. J Exp Med 184:1435-1447.
28. Feng, D., J. A. Nagy, K. Pyne, H. F. Dvorak, and A. M. Dvorak. 1998. Neutrophils emigrate from venules by a transendothelial cell pathway in response to fMLP. J. Exp. Med. 187:903-915.
29. Ali, J., F. Liao, E. Martens, and W. A. Muller. 1997. Vascular endothelial cadherin (VE-Cadherin): Cloning and role in endothelial cell-cell adhesion. Microcirculation 4:267-277.
30. Lampugnani, M. G., M. Resnati, M. Raiteri, R. Pigott, A. Piscane, G. Houen, L. P. Ruco, and E. Dejana. 1992. A novel endothelial-specific membrane protein is a marker of cell-cell contacts. J. Cell. Biol. 118:1511-1522.
31. Gotsch, U., E. Borges, R. Bosse, E. Boggemeyer, M. Simon, H. Mossmann, and D. Vestweber. 1997. VE-cadherin antibody accelerates neutrophil recruitment in vivo. J. Cell Sci. 110:583-588,
32. de Fougerolles, A. R., S. A. Stacker, R. Schwarting, and T. A. Springer. 1991. Characterization of ICAM-2 and evidence for a third counter-receptor for LFA-1. J. Exp. Med. 174:253-267.
33. Xu, H., I. L. Tong, A. R. de Fougerolles, and T. A. Springer. 1992. Isolation, characterization, and expression of mouse ICAM-2 complementary and genomic DNA. J. Immunol. 149:2650-2655.
34. Xie, J., R. Li, P. Kotovuri, C. Vermot-Desroches, J. Wijdenes, M. Arnaout, P. Nortamo, and C. G. Gahmberg. 1995. Intercellular adhesion molecule-2 (CD102) binds to the leukocyte integrin CD11b/CD18 through the A domain. J. Immunol. 155:3619-3628.
35. Martin-Padura, I., S. Lostaglio, M. Schneemann, L. Williams, M. Romano, P. Fruscella, C. Panzeri, A. Stoppacciaro, L. Ruco, A. Villa, D. Simmons, and E. Dejana. 1998. Junctional adhesion molecule, a novel member of the immunoglobulin superfamily that distributes at intercellular junctions and modulates monocyte transmigration. J. Cell Biol. 142:117-127.
36. Naik, U. P., Y. H. Ehrlich, and E. Kornecki. 1995. Mechanisms of platelet activation by a stimulatory antibody: Cross-linking of a novel platelet receptor for monoclonal antibody F11 with the FcgammaRII receptor. Biochem. J. 310:155-162.
37. Furuse, M., T. Hirase, M. Itoh, A. Nagafuchi, S. Yonemura, S. Tsukita, and S. Tsukita. 1993. Occludin: A novel integral membrane protein localizing at tight junctions. J. Cell Biol. 123:1777-1788.
38. McCarthy, K. M., I. B. Skare, M. C. Stankewich, M. Furuse, S. Tsukita, R. A. Rogers, R. D. Lynch, and E. E.

Schneeberger. 1996. Occludin is a functional component of the tight junction. J. Cell Sci. 109:2287-2298.

39. Fujimoto, K. 1995. Freeze-fracture replica electron microscopy combined with SDS digestion for cytochemical labeling of integral membrane proteins. Application to the immunogold labeling of intercellular junctional complexes. J. Cell Sci. 108:3443-3449.

40. Saitou, M., K. Fujimoto, Y. Doi, M. Itoh, T. Fujimoto, M. Furuse, H. Takano, T. Noda, and S. Tsukita. 1998. Occludin-deficient embryonic stem cells can differentiate into polarized epithelial cells bearing tight junctions. J. Cell Biol. 141:397-408.

41. Furuse, M., K. Fujita, T. Hiiragi, K. Fujimoto, and S. Tsukita. 1998. Claudin-1 and -2: Novel integral membrane proteins localizing at tight junctions with no sequence similarity to occludin. J. Cell Biol. 141:1539-1550.

42. Morita, K., H. Sasaki, K. Fujimoto, M. Furuse, and S. Tsukita. 1999. Claudin-11/OSP-based tight junctions of myelin sheaths in brain and sertoli cells in testis. J. Cell Biol. 145:579-588.

43. Morita, K., M. Furuse, K. Fujimoto, and S. Tsukita. 1999. Claudin multigene family encoding four-transmembrane domain protein components of tight junction strands. Proc. Natl. Acad. Sci. USA 96:511-516.

44. Muller, W. A. 1996. Transendothelial migration of leukocytes. In Leukocyte recruitment in inflammatory disease. G. Peltz, editor. R.G. Landis Company, Austin, Tex. 3-18.

45. Muller, W. A. and S. Weigl. 1992. Monocyte-selective transendothelial migration: Dissection of the binding and transmigration phases by an in vitro assay. J. Exp. Med. 176:819-828.

46. Butcher, E. C. 1991, Leukocyte-endothelial cell recognition: three (or more) steps to specificity and diversity. Cell 67:1033-1036.

47. Carlos, T. M. and J. M. Harlan. 1994. Leukocyte-Endothelial Cell Adhesion Molecules. Blood 84:2068-2101.

48. Muller, W. A., C. M. Ratti, S. L. McDonnell, and Z. A. Cohn. 1989. A human endothelial cell-restricted, externally disposed plasmalemmal protein enriched in intercellular junctions. J. Exp. Med. 170:399-414.

49. Albelda, S. M., W. A. Muller, C. A. Buck, and P. J. Newman. 1991. Molecular and cellular properties of PECAM-1 [endoCAM/CD31]: A novel vascular cell-cell adhesion molecule. J. Cell Biol. 114:1059-1068.

50. Muller, W. A. 1992. PECAM-1: an adhesion molecule at the junctions of endothelial cells. In Mononuclear Phagocytes. The Proceedings of the Fifth Leiden Meeting on Mononuclear Phagocytes. R. van Furth, Z. A. Cohn, and S. Gordon, editors. Blackwell Publishers, London. 138-148.

51. Shang, X. Z. and A. C. Issekutz. 1998. Contribution of CD11a/CD18, CD11b/CD18, ICAM-1 (CD54) and -2 (CD102) to human monocyte migration through endothelium and connective tissue fibroblast barriers. Eur. J. Immunol. 28:1970-1979.

52. Issekutz, A. C., D. Rowter, and T. A. Springer. 1999. Role of ICAM-1 and ICAM-2 and alternate CD11/CD18 ligands in neutrophil transendothelial migration. J. Leuk. Biol. 65:117-126.

53. Xie, Y. and W. A. Muller. 1993. Molecular cloning and adhesive properties of murine platelet/endothelial cell adhesion molecule-1. Proc. Natl. Acad. Sci. USA 90:5569-5573.

54. Kostrikis, L. G., Y. Huang, J. P. Moore, S. M. Wolinsky, L. Zhang, Y. Guo, L. Deutsch, J. Phair, A. U. Neumann, and D. D. Ho. 1998. A chemokine receptor CCR2 allele delays HIV-1 disease progression and is associated with a CCR5 promoter mutation. Nat. Med. 4:350-353.

55. McElrath, M. J., G. Kaplan, A. Nusrat, and Z. A. Cohn. 1987. Cutaneous leishmaniasis. The defect in T cell influx in BALB/c mice. J. Exp. Med. 165:546-559.

56, Smith, C. W., T. K. Kishimoto, O. Abbass, B. Hughes, R. Rothlein, L. V. McIntire, E. Butcher, and D. C. Anderson. 1991. Chemotactic factors regulate lectin adhesion molecule 1 (LECAM-1)-dependent neutrophil adhesion to cytokine-stimulated endothelial cells in vitro. J. Clin. Invest. 87:609-618.

57. Muller, W. A., R. M. Steinman, and Z. A. Cohn. 1980. The membrane proteins of the vacuolar system. I. Analysis by a novel method of intralysosomal iodination. J. Cell Biol. 86:292-303.

58. Muller, W. A., R. M. Steinman, and Z. A. Cohn. 1980. The membrane proteins of the vacuolar system. II. Bidirectional flow between secondary lysosomes and plasma membrane. J. Cell Biol. 86:304-314.

59. Muller, W. A. and M. A. Gimbrone Jr. 1986. Plasmalemmal proteins of cultured vascular endothelial cells exhibit apical-basal polarity: Analysis by surface-selective iodination. J. Cell Biol. 103:2389-2402.

60. Pober, J. S., M. P. Bevilacqua, D. L. Mendrick, L, A. Lapierre, W. Fiers, and M. A. Gimbrone. 1986. Two distinct monokines, interleukin 1 and tumor necrosis factor, each independently induce biosynthesis and transient expression of the same antigen on the surface of cultured human vascular endothelial cells. J. Immunol. 136:1680-1687.

61. Romer, L. H., N. V. McLean, Y. Horng-Chin, M. Daise, J. Suns and H. M. Delisser. 1995. IFN-gamma and TNF-alpha induce redistribution of PECAM-1 [CD31] on human endothelial cells. J. Immunol. 154:6582-6592.

62. Aruffo, A. and B. Seed. 1987. Molecular cloning of CD28 cDNA by a high-efficiency COS cell expression system. Proc. Natl. Acad. Sci. USA 84:8573-8577.

63. Seed, B. and A. Aruffo. 1987. Molecular cloning of the CD2 antigen, the T-cell erythrocyte receptor, by a rapid immunoselection procedure. Proc. Natl. Acad. Sci. USA 84:3365-3369.

64. Maniatis, T., E. F. Fritsch, and J. Sambrook, 1982. Molecular Cloning: A Laboratory Manual. Anonymous Cold Spring Harbor Laboratories, Cold Spring Harbor, N.Y. 191-192.

65. Muller, W. A., M. E. Berman, P. J. Newman, H. M. Delisser, and S. M. Albelda. 1992. A heterophilic adhesion mechanism for Platelet/Endothelial Cell Adhesion Molecule-1 [CD31]. J. Exp. Med. 175:1401-1404.

66. Huang, A. J., J. E. Manning, T. M. Bandak, M. C. Ratau, K. R. Hanser, and S. C. Silverstein. 1993. Endothelial cell cytosolic free calcium regulates neutrophil migration across monolayers of endothelial cells. J. Cell Biol. 120:1371-1380.

67. DiVirgilio, F., T. H. Steinberg, J. A. Swanson, and S. C. Silverstein. 1988. Fura-2 secretion and sequestration in macrophages. J. Immunol. 140:915-920.

68. Galfre, G., S. C. Howe, C. Milstein, G. N. Butcher, and J. C. Howard. 1977. Antibodies to major histocompatibility antigens produced by hybrid cell lines. Nature 266:550-552.

69. Mishell, B. B. and S. M. Shiigi. 1980. Selected methods in cellular immunology. W.H. Freeman, San Francisco.

70. Reilly, P. L., J. R. J. Woska, D. D. Jeanfavre, E. McNally, R. Rothlein, and B. J. Bormann. 1995. The native structure of intercellular adhesion molecule-1 (ICAM-1) is a dimer. Correlation with binding to LFA-1. J. Immunol. 155:529-532.

71. Miller, J., R. Knorr, M. Ferrone, R. Houdei, C. P. Carron, and M. L. Dustin. 1995. Intercellular adhesion molecule-1 dimerization and its consequences for adhesion mediated by lymphocyte function associated molecule-1. J Exp Med 182:1231-1241.

72. Mizgerd, J. P., H. Kubo, G. J. Kutkoski, S. D. Bhagwan, K. Scharffeter-Kochanek, A. L. Beaudet, and C. M. Doerschuk. 1997. Neutrophil emigration in the skin, lungs, and peritoneum: Different requirements for CD11/CD18 revealed by CD18-deficient mice. *J. Exp. Med.* 186:1357-1364.
73. Mayadas, T. N., R. C. Johnson, H. Rayburn, R. O. Hynes, and D. D. Wagner. 1993. Leukocyte rolling and extravasation are severely compromised in P selectin-deficient mice. *Cell* 74:541-554.
74. Watson, S. R., C. Fennie, and L. A. Lasky. 1991. Neutrophil influx into an inflammatory site inhibited by a soluble homing receptor-IgG chimaera. *Nature* (London) 349:164-167.
75. Muller W A, C M Ratti, S L McDonnell, Z A Cohn. 1989. A human endothelial cell-restricted, externally disposed plasmalemma protein enriched in intercellular junctions. *J. Exp. Med.* 170, 399-414.
76. Muller W A, M E Berman, P J Newman, H M Delisser, and S M Albelda. 1992. A heterophilic adhesion mechanism for platelet/endothelial cell adhesion molecule-1 (CD31). *J. Exp. Med.* 175:1401-1404.
77. Schenkel A R, Z Mamdouh, X Chen, R M Liebman, W A Muller. 2002. CD99 plays a major role in the migration of monocytes through endothelial junctions. *Nature Immunol.* 3:143-150.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all values are approximate, and are provided for description.

All patents, applications, publications, test methods, literature, and other materials cited herein are hereby incorporated by reference for all purposes, including the preceding text for which it was cited.

What is claimed:

1. A method of inhibiting transendothelial migration (TEM) of neutrophils and monocytes, which method comprises contacting the neutrophils and monocytes with an anti-CD99L2 antibody to thereby inhibit CD99L2-mediated neutrophil and monocyte transmigration through endothelium.

2. The method according to claim 1, wherein CD99L2 is located on endothelial cells.

3. The method according to claim 1, wherein CD99L2 is located on the neutrophils and monocytes.

4. The method according to claim 1 wherein TEM is inhibited between activated endothelial cells.

5. The method according to claim 4, wherein the activated endothelial cells are activated as a result of contact with a pro-inflammatory cytokine selected from the group consisting of tumor necrosis factor (TNF) and interleukin-1 (IL-1).

6. The method according to claim 1, wherein the endothelium is excised endothelial tissue maintained in a tissue culture.

7. The method according to claim 1, wherein the endothelium is cultured on a permeable membrane in vitro.

8. The method according to claim 1, wherein the endothelium comprises human umbilical vein endothelial cells (HUVEC).

9. The method according to claim 1, wherein the TEM is inhibited across endothelial cells in a tissue selected from the group consisting of arterial endothelium, venous endothelium, venous endothelium, and post-capillary venular endothelium.

10. The method according to claim 1, wherein TEM is inhibited into a site of inflammation.

11. The method according to claim 1, wherein inhibiting CD99L2-mediated transmigration of neutrophils and monocytes comprises contacting the neutrophils, monocytes or the endothelium with the anti-CD99L2 antibody.

12. The method according to claim 1, wherein the anti-CD99L2 antibody is a monoclonal antibody to CD99L2.

13. A method of inhibiting CD99L2-mediated transendothelial migration in vivo within a patient having an inflammatory condition, which method comprises administering to the patient a therapeutically effective dosage of an anti-CD99L2 antibody to thereby inhibit CD99L2-mediated neutrophil or monocyte transendothelial migration (TEM) into a site of inflammation within a patient.

14. The method according to claim 13, wherein the TEM occurs across endothelial cells in a tissue selected from the group consisting of arterial endothelium, venous endothelium, capillary endothelium, venular endothelium, and post-capillary venular endothelium.

15. The method according to claim 13, wherein the inflammatory condition is an acute inflammatory condition.

16. The method according to claim 13, wherein the inflammatory condition results from an infection.

17. The method according to claim 13, wherein the inflammatory condition is a chronic inflammatory condition.

18. The method according to claim 13, wherein CD99L2-mediated TEM is inhibited by intracerebral, intradermal, intramuscular, intraperitoneal, intravenous, subcutaneous or intranasal administration of the anti-CD99L2 antibody.

19. The method according to claim 13, wherein the anti-CD99L2 antibody is an anti-CD99L2 monoclonal antibody.

20. The method of claim 13, wherein the anti-CD99L2 antibody inhibits neutrophil or monocyte migration into the site of inflammation within the patient.

21. The method of claim 13, wherein the anti-CD99L2 antibody is a humanized anti-CD99L2 monoclonal antibody.

22. The method of claim 13, wherein the inflammatory condition is atherosclerosis, an autoimmune condition, multiple sclerosis, systemic lupus erythematosus, polymyalgia rheumatica, rheumatoid arthritis, Sjogren's Syndrome, scleroderma, ankylosing spondylitis, polymyositis, dermatomyositis, pemphigus, pemphigoid, Type I diabetes mellitus, myasthenia gravis, Hashimoto's thyroiditis, Graves' disease, Goodpasture's disease, mixed connective tissue disease, sclerosing cholangitis, inflammatory bowel disease, Crohn's Disease, ulcerative colitis, pernicious anemia, inflammatory dermatoses, usual interstitial pneumonitis (UIP), asbestosis, silicosis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis, angiitis, temporal arteritis, polyarteritis nodosa, inflammatory dermatoses, chronic active hepatitis, a delayed-type hypersensitivity reaction, poison ivy dermatitis, pneumonia, respiratory tract inflammation, Adult Respiratory Distress Syndrome (ARDS), encephalitis, inflammatory edema, immediate hypersensitivity reaction, asthma, hay fever, cutaneous allergy, acute anaphylaxis, rheumatic fever, acute glomerulonephritis, chronic glomerulonephritis, post-infectious glomerulonephritis, post-Streptococcal glomerulonephritis, systemic lupus erythematosus, pyelonephritis, cellulitis, cystitis, acute cholecystitis, transient ischemia, sequelae of organ transplantation, tissue allograft inflammation, allogeneic organ transplantation inflammation, allogeneic tissue transplantation inflammation, or chronic host-versus-graft rejection.

\* \* \* \* \*